United States Patent
Aujla et al.

(10) Patent No.: US 7,557,130 B2
(45) Date of Patent: *Jul. 7, 2009

(54) BICYCLIC HETEROAROMATIC ALANINES

(75) Inventors: Pavandeep Aujla, Hayes (GB); Timothy John Norman, Great Missenden (GB); John Robert Porter, Chinnor (GB); Stuart Bailey, Dorking (GB); Stephen Brand, Reading (GB)

(73) Assignee: UCB Pharma, S.A. (BE)

( * ) Notice: Subject to any disclaimer, the term of this patent is extended or adjusted under 35 U.S.C. 154(b) by 846 days.

This patent is subject to a terminal disclaimer.

(21) Appl. No.: 10/484,552

(22) PCT Filed: Jul. 25, 2002

(86) PCT No.: PCT/GB02/03400

§ 371 (c)(1),
(2), (4) Date: Apr. 29, 2004

(87) PCT Pub. No.: WO03/011815

PCT Pub. Date: Feb. 13, 2003

(65) Prior Publication Data

US 2004/0209913 A1    Oct. 21, 2004

(30) Foreign Application Priority Data

Jul. 26, 2001    (GB) ................ 0118241.9
Nov. 6, 2001    (GB) ................ 0126653.5

(51) Int. Cl.
*A61K 31/44* (2006.01)
*C07D 401/00* (2006.01)

(52) U.S. Cl. .................. 514/339; 546/277.4
(58) Field of Classification Search ............ 548/266.2; 514/383, 339; 546/277.4
See application file for complete search history.

(56) References Cited

U.S. PATENT DOCUMENTS 3,938,367 A    2/1976    Fletcher et al. ............... 73/28
2007/0027174 A1*    2/2007    Brand et al. .................. 514/278

FOREIGN PATENT DOCUMENTS

| WO | WO 99/64390 | 12/1999 |
| WO | WO 00/15612 | 3/2000 |
| WO | WO 00/23419 A1 | 4/2000 |
| WO | WO 00/73260 A1 | 12/2000 |
| WO | WO 01/79173 A2 | 10/2001 |

OTHER PUBLICATIONS

Abraham, W.M., et al., "$\alpha_4$-integrins mediate antigen-induced late bronchial responses and prolonged airway hyperresponsiveness in sheep." *J. Clin. Invest.*, 1994, 93, 776-787.

Alhaique, F., et al., "Cyclisation of dinitriles by sodium alkoxides a new synthesis of naphthyridines," *Tetrahedron Lett.*, 1995, 3, 173-174.

Ames, D.E., et al., "Condensation of β-dicarbonyl compounds with halogenopyridinecarb-oxylic acids. A convenient synthesis of some naphthyridine derivatives," *J. Chem. Soc. Perkin*, 1972, 1, 705-710.

Baldwin, J., et al., "A novel naphthyridinone synthesis via enamine cyclization," *J. Org. Chem.*, 1978, 43(25), 4878-4880.

Berlin, C., et al., "α4β integrin mediates lymphocyte binding to the mucosal vascular addressin MAdCAM-1," *Cell*, 1993, 74, 185-195.

Binns, R.M., et al., "The role of E-selectin in lymphocyte and polymorphonuclear cell recruitment into cutaneous delayed hypersensitivity reactions in sensitized pigs," *J. Immunol.*, 1996, 157, 4094-4099.

Bodor, N., "Novel approaches in prodrug design," *Alfred Benzon Symposium*, 1982, 17, 156-177.

Bordner, J., et al., "1,3-diamino-6,7-dimethoxyisoquinoline derivatives as potential $\alpha_1$-adrenoceptor," *J. Med. Chem.*, 1988, 31, 1036-1039.

Briskin, M.J., et al., "Structural requirements for mucosal vascular addressin binding to its lymphocyte receptor $\alpha_4\beta_7$," *J. Immunol.*, 1996, 156, 719-726.

Brooks, P.C., et al., "Antiintegrin αvβ3 blocks human breast cancer growth and angiogenesis in human skin," *J. Clin. Invest.*, 1995, 96, 1815-1822.

Brun, E.M., et al., "Dienediolates of α,β-unsaturated carboxylic acids in synthesis: a new synthetic method to 2-pyridones," *Synlett*, 1999, 07, 1088-1090.

Brun, E.M., et al., "A new synthetic method to 2-pyridones," *Synthesis*, 2000, 2, 273-280.

Bundgaard, H., Design of Prodrugs, *Elsevier, Amsterdam*, 1985.

(Continued)

*Primary Examiner*—Janet L Andres
*Assistant Examiner*—Binta M Robinson
(74) *Attorney, Agent, or Firm*—McDonnell Boehnen Hulbert & Berghoff LLP

(57) ABSTRACT

Compounds of formula (1) are described: in which X is an —O— or —S— atom or —N(R$^2$)— group and R$^1$ is a group Ar$^1$L$^2$Ar$^2$Alk- in which Ar$^1$ is an optionally substituted aromatic or heteroaromatic group, L$^2$ is a covalent bond or a linker atom or group, Ar$^2$ is an optionally substituted bicyclic heteroarylene group and Alk is a chain —CH$_2$—CH(R)—, —CH=C(R)—, OR—CH(CH$_2$R)— in which R is a carboxylic acid (—CO$_2$H) or a derivative or biostere thereof. The compounds are selective inhibitors of alpha 4 integrins such as $\alpha_4\beta_1$ and are of use in modulating cell adhesion for the prophylaxis or treatment of inflammatory diseases or disorders, such as rheumatoid arthritis, in which the extravasculation of leukocytes plays a role.

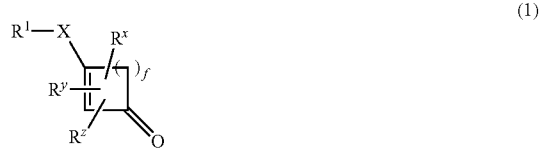

(1)

13 Claims, No Drawings

OTHER PUBLICATIONS

Cardarelli, P.M., et al., "Cyclic RGD peptide inhibits α4β1 interaction with connecting segment 1 and vascular cell adhesion molecule," *J. Biol. Chem.*, 1994, 269(28), 18668-18673.

Deady, L.W., et al., "Ethoxycarbonylation of α-cyano-*o*-toluonitrile and cyclization to isoquinolines and pyrimido[4,5-*c*]isoquinolines," *Aust. J. Chem.*, 1989, 42, 1029-1034.

Erle, D.J., et al., "Expression and function of the MAdCAM-1 receptor, integrin α4β7, on human leukocytes," *J. Immunol.*, 1994, 153, 517-528.

Ezcurra, J.E., et al., "Synthesis of o-quinodimethanes and benzocyclobutenes from dimethyl squarate," *Tetrahedron Letts.*, 1993, 34(39), 6177-6180.

Falk, H., et al., "On the chemistry of pyrrole pigments, XCI [1]: copper complexes of pyridinologous linear tri- and tetra-pyrroles as cyclopropanation catalysts," *Monatsch. Für Chemie.*, 1994, 25, 325-333.

Ferguson, T.A., et al., "Two integrin-binding peptides abrogate T cell-mediated immune responses in vivo," *PNAS*, 1991, 88, 8072-8076.

Fieser and Fieser's Reagents for Organic Synthesis, *John Wiley and Sons*, 1999, vols. 1-19.

Giacomello, G., et al., "Synthesis of 2,6-naphthyridine," *Tetrahedron Lett.*, 1965, 1117-1121.

Green, T.W., in Protective Groups in Organic Synthesis, *John Wiley & Sons*, 1999.

Hammes, H.-P., et al., "Subcutaneous injection of a cyclic peptide antagonist of vitronectin receptor-type integrins," *Nature Medicine*, 1996, 529-533.

Heileman, M.J., et al., "New metathesis methodololgy leading to angularly-fused polycyclic quinines and related compounds," *J. Am. Chem. Soc.*, 1998, 120, 3801-3802.

Hergueta, R.A., et al., "Rearrangements of cyclobutenones. Synthesis of *N*-methyl-7,8-dihydrobenzophenanthridine-9,12-diols and related compounds," *J. Org. Chem.*, 1999, 64, 5979-5983.

Hesterberg, P.E., et al., "Rapid resolution of chronic colitis in the cotton-top tamarin with an antibody to a gut-homing integrin α4β7," *Gastroenterol*, 1996, 111, 1373-1380.

Hiebl, J., et al., "new synthesis of isoquinoline-3-carboxylates," *Tetrahedron Lett.*, 1999, 40, 7935-7938.

Hodivala-Dilke, K.M., "β3-integrin-deficient mice are a model for glanzmann thrombasthenia," *J. Clin. Invest.*, 1999, 103(2), 229-238.

Holzmann, B., et al., "Peyer's patch-specific lymphocyte homing receptors consist of a VLA-4like α chain associated with either of two integrin β chains, one of which is novel," *EMBO J.*, 1989, 8(6), 1735-1741.

Humphries, M.J., et al., "Mechanisms of VCAM-1 and fibronectin binding to integrin α4β1: implications for integrin function and rational drug design," *Ciba Foundation Symposium*, 1995, 189, 177-194.

Issekutz, T.B., "Inhibition of lymphocyte endothelial adhesion and in vivo lymphocyte migration to cutaneous inflammation by TA-3, a new monoclonal antibody to rat LFA-1," *J. Immunol.*, 1992, 149(10), 3394-3402.

Kaiser, E.M., et al., "Facile synthesis of 1-amino-3-arylisoquinolines," *Synthesis*, 1974, 11, 805-806.

Katritzky, et al. (Ed.), Comprehensive Heterocyclic Chemistry, *Pergamon*, 1984, vols. 1-8.

Katritzky, et al. (Ed.), Comprehensive Heterocylic Chemistry, *Pergamon*, 1994, vols. 1-11.

Katritzky, et al. (Ed.), Comprehensive Organic Functional Group Transformations, *Pergamon*, 1995, vols. 1-7.

Kraus, J.-L., et al., "Sur la reactivite du squarate de dimethyle vis-á-vis de thiols," *Tetrahedron Lett.*, 1987, 28(16), 1765-1768 (French only).

Larock's Comprehensive Organic Transformations, *VCH Publishers*, 1989.

Li, Z., et al., "Effect of an anti-Mo1 MAb on ozone-induced airway inflammation and airway hyperresponsiveness in dogs," *Am. J. Physiol.*, 1992, 263, L723-L726.

MacDougall, J.M., et al., "Rearrangements of linear triquinanes to the angular isomers," *J. Org. Chem.*, 1999, 64, 7445-7450.

March's Advanced Organic Chemistry, 5$^{th}$ Ed., *John Wiley and Sons*, 2001.

Marlin, S.D., et al., "LFA-1 immunodeficiency disease: Definition of the geneticdefect and chromosomal mapping of α and β subunits of the lymphocyte function-associated antigen 1 (LFA-1) by complementation in hybrid cells," *J. Exp. Med.*, 1986, 164, 855-867.

Mitjan, F., et al., "An anti-αv-integrin antibody that blocks integrin function inhibits the development of a human melanoma in nude mice," *J. Cell Sci.*, 1995, 108, 2825-2838.

Molina, P., et al., "iminophosphorane-mediated annelation of a pyridine ring into a preformed pyridine one: synthesis of naphthyridine, pyrido[1,2-c] pyrimidine and pyrido[1,2-c]quinazoline derivatives," *Tetrahedron*, 1992, 48(22), 4601-4616.

Molino, P., et al., "Preparation and thermal ring-closure of β-aryl vinyl carbodi-imides: synthesis of isoquinoline derivatives," *J. Chem. Soc. Perkin Trans.*, 1990, 1, 1727-1731.

Nagarajan, A., et al., "Organopalladium mediated synthesis of isocarbostyrils," *Indian J. Chem.*, 1989, 28B, 67-78.

Newman, P., et al., "Integrin adhesion receptors: structure, function and implications for biomedicine," *Molecular Medicine Today*, 1996, 304-313.

Numata, A., et al., "General synthetic method for naphthyridines and their *N*-oxides containing isoquinolinic nitrogen," *Synthesis*, 1999, 2, 306-311.

Ohno, M., et al., "Synthesis of γ-acylmethylenetetronates from squaric acid," *Tetrahedron Lett.*, 1993, 34(30), 4807-4810.

Osborne, L., "Leukocyte adhesion to endothelium in inflammation," *Cell*, 1990, 62, 3-6.

Paquette, (Ed.), Encyclopedia of Reagents for Organic Synthesis, *John Wiley and Sons*, 1995, vols. 1-8.

Petasis, N.A., et al., "Synthesis of substituted benzonorbornadines from cyclobutenediones," *Synlett*, 1996, 155-156.

Petasis, N.A., et al., "Titanium-mediated olefinations of cyclobutenedione derivatives," *Tetrahedron Lett.*, 1995, 36(34), 6001-6004.

Podolsky, D.K., et al., "Attenuation of colitis in the cotton-top tamarin by anti-α4 integrin monoclonal antibody," *J. clin. Invest.*, 1993, 92, 372-380.

Rodd's Chemistry of Carbon Compounds, *Elsevier Science Publishers*, 1989, vols. 1-15 and Supplementals.

Sakamoto, T., et al., "Condensed heteroaromatic ring systems. III. Synthesis of naphthyridine derivatives by cyclization of ethynylpyridinecarboxamides," *Chem. Pharm. Bull.*, 1985, 33(2), 626-633.

Sheffield, D.J., "Synthesis of some 4-pyridylpyruvic acids as potential lactate dehydro-genase inhibitors," *J. Chem. Soc. Perkin. Trans.*, 1972, 1, 2506-2509.

Shorff, H.N.,et al. "Small peptide inhibitors of α4β7 mediated MAdCAM-1 adhesion to lymphocytes," *Biorganic Med. Chem. Lett.*, 1996, 6, 2495-2500.

Singh, G., et al., "Prodrug approach in new drug design and development," *J. Sci. Ind. Res.*, 1996, 55, 497-510.

Sonneberg, A., "Integrins and their ligands," *Current Topics in Microbiology and Immunology*, 1993, 184, 7-35.

Springer, T.A., "Traffic signals for lymphocyte recirculation and leukocyte emigration: the multistep paradigm," *Cell*, 1994, 76, 301-314.

Springer, T.A., "Adhesion receptors of the immune system," *Nature*, 1990, 346, 425-434.

Srivata, S., et al., "Selective αvβ3 integrin blockade potently limits neointimal hyperplasia and lumen stenosis following deep coronary arterical stent injury evidence for the functional importance of integrin αvβ3 and osteopontin expression during neointima formation," *Cardiovascular Res.*, 1997, 36, 408-428.

Tan, R., et al., "Synthesis of 2,6-naphthyridine and some of its derivatives," *Tetrahedron Lett.*, 1965, 2737-2744.

Tovar, J.D., et al., "Pyrylium salts via electrophilic cyclization: applications for novel 3-arylisoquinoline systheses," *J. Org. Chem.*, 1999, 64, 6499-6504.

Trost, et al. (Eds.), Comprehensive Organic Synthesis, *Pergamon*, 1991, vol. 1-9.

Turnbull, P., et al., "regioselective synthesis of highly substituted naphthols," *J. Org. Chem.*, 1995, 60, 644-649.

Vanderslice, P., et al., "A cyclic hexapeptide is a potent antagonist of α₄ integrins," *J. Immunol.*, 1997, 158, 1710-1718.

Wenkert E., et al., "4-acylmethylnicotinonitrile derivatives," *Aust. J. Chem.*, 1972, 25, 433-438.

Wenkert, E., et al., "General methods of synthesis of indole alkaloids. VI. Syntheses of *dl*-corynantheidine and a camptothecin model," *J. Am. Chem. Soc.*, 1967, 89, 6741-6745.

Wu, M.-J., et al., "A direct anionic cyclization of 2-alkynylbenzonitrile to 3-substituted-1(2*H*)-isoquinolones and 3-benzylideneisoindol-2-ones initiated by methoxide addition," *Tetrahedron*, 1999, 55, 13193-13200.

Xu, S.L., et al., "Synthesis of *p*-chlorophenols (and -naphthols) from the thermal rearrangement of 4-chlorocyclobutenones," *J. Org. Chem.*, 1992, 57, 326-328.

Yamamoto, Y., et al., "2-[1-(trimethylsily)alkylidene]-4-cyclopentene-1.3-dione from Lewis acid-catalyzed reaction of cyclobutenedionemonoacetal with alkynylsilane: novel cationic 1,2-silyl migrative ring opening and subsequent 5-exo-*trig* ring closure," *J. Org. Chem.*, 1997, 62, 1292-1298.

Yang, X.-D., et al., "A predominant role of integrin α₄ in the spontaneous development of autoimmune diabetes in nonobese diabetic mice," *PNAS*, 1994, 91, 12604-12608.

Yednock, T.A., et al., "Prevention of experimental autoimmune encephalomyelitis by antibodies against α4β1 integrin," *Nature*, 1992, 356, 63-66.

Yerxa, B.R., et al., "Synthesis of indolizine-5,8-diones and [3,2.2]cyclazines," *Tetrahedron Lett.*, 1992, 33(51), 7811-7814.

Yerxa, B.R., et al., "Synthesis of (±)-septicine," *Tetrahedron*, 1994, 50(21), 6173-6180.

Zhag, D., et al., "A versatile synthesis of 3-substituted indolines and indoles," *J. Org. Chem.*, 1996, 61, 2594-2595.

\* cited by examiner

BICYCLIC HETEROAROMATIC ALANINES

This invention relates to a series of bicyclic heteroaromatic alanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin $\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H.-P. et al, Nature Medicine 2, 529, (1996); Srivata, S. et al, Cardiovascular Res. 36, 408 (1997)]. In particular an anti $\alpha_4\beta_7$-antibody has demonstrated both clinical and histologic improvement of inflammatory activity and disease in a non-human primate model of inflammatory bowel disease [Hesterberg, P. E. et al, Gastroenterol, 111, 1373-80 (1996)]. A number of monoclonal antibodies which block integrin function are currently being investigated for their therapeutic potential in human disease, and one, ReoPro, a chimeric antibody against the platelet integrin $\alpha$IIb$\beta$3 is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the $\alpha 4$ chain which can pair with two different beta chains $\beta 1$ and $\beta 7$ [Sonnenberg, A., ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erie, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue such as gastrointestinal mucosa termed MAdCAM-1 [Berlin, C. et al, Cell, 74, 185, (1993)]. MAdCAM-1 is preferentially expressed in the gastointestinal track. The interaction between $\alpha 4\beta 7$ and MAdCAM-1 may also be important sites of inflammation outside of mucosal tissue [Yang, X.-D. et al, PNAS, 91, 12604, (1994)].

Regions of the peptide sequence recognizeded by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha 4\beta 1$ and/or $\alpha 4\beta 7$ at concentrations at which they generally have no or minimal inhibitory action on a integrins of other subgroups. These compounds possess the additional advantage of good pharmacokinetic properties, especially low plasma clearance.

Thus according to one aspect of the invention we provide a compound of formula (1):

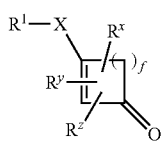

wherein
R$^1$ is a group Ar$^1$L$^2$Ar$^2$Alk- in which:
Ar$^1$ is an optionally substituted aromatic or heteroaromatic group;
L$^2$ is a covalent bond or a linker atom or group;
Ar$^2$ is an optionally substituted bicyclic heteroarylene group;
and Alk is a chain

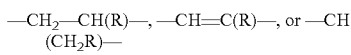

in which R is a carboxylic acid (—CO$_2$H) or a derivative or biostere thereof;
X is an —O— or —S— atom or —N(R$^2$)— group in which:
R$^2$ is a hydrogen atom or a C$_{1-6}$alkyl group;
R$^x$, R$^y$ and R$^z$ which may be the same or different is each an atom or group —L$^1$(Alk$^1$)$_n$(R$^3$)$_v$ in which L$^1$ is a covalent bond or a linker atom or group, Alk$^1$ is an optionally substituted aliphatic or heteroaliphatic chain, R$^3$ is a hydrogen or halogen atom or group selected from —OR$^{3a}$ [where R$^{3a}$ is a hydrogen atom or an optionally substituted straight or branched C$_{1-6}$alkyl group or C$_{3-8}$cycloalkyl group], —SR$^{3a}$, —CN or an optionally substituted cycloaliphatic, heterocycloaliphatic, polycycloaliphatic, heteropolycyclo-aliphatic, aromatic or heteroaromatic group, n is zero or the integer 1 and v is the integer 1, 2 or 3 provided that when n is zero and L$^1$ is a covalent bond v is the integer 1; or R$^z$ is an atom or group as previously defined and R$^x$ and R$^y$ are joined together to form an optionally substituted spiro linked cycloaliphatic or heterocycloaliphatic group;
f is the integer 1, 2, 3 or 4;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto (CH$_2$C═O)-enol (CH═CHOH) tautomers. Formula (1) and the formulae hereinafter are intended to represent all individual tautomers and mixtures thereof, unless stated otherwise.

Optionally substituted aromatic groups represented by Ar$^1$ when present in the group R$^1$ include for example optionally substituted monocyclic or bicyclic fused ring C$_{6-12}$ aromatic groups, such as phenyl, 1- or 2-naphthyl, 1- or 2-tetrahydronaphthyl, indanyl or indenyl groups.

Optionally substituted heteroaromatic groups represented by the group Ar$^1$ when present in the group R$^1$ include for example optionally substituted C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, e.g. 2,6-naphthyridinyl, or 2,7-naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl groups.

Each aromatic or heteroaromatic group represented by the group Ar$^1$ may be optionally substituted on any available carbon or, when present, nitrogen atom. One, two, three or more of the same or different substituents may be present and each substituent may be selected for example from an atom or group —L$^3$(Alk$^2$)$_t$L$^4$(R$^4$)$_u$ in which L$^3$ and L$^4$, which may be the same or different, is each a covalent bond or a linker atom or group, t is zero or the integer 1, u is an integer 1, 2 or 3, Alk$^2$ is an optionally substituted aliphatic or heteroaliphatic chain and R$^4$ is a hydrogen or halogen atom or a group selected from optionally substituted C$_{1-6}$alkyl or C$_{3-8}$cycloalkyl, —OR$^5$ [where R$^5$ is a hydrogen atom, an optionally substituted C$_{1-6}$alkyl or C$_{3-8}$cycloalkyl group], —SR$^5$, —NR$^5$R$^6$ [where R$^6$ is as just defined for R$^5$ and may be the same or different], —NO$_2$, —CN, —CO$_2$R$^5$, —SO$_3$H, —SOR$^5$, —SO$_2$R$^5$, —SO$_3$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$) [where R$^7$ is a hydrogen atom, an optionally substituted C$_{1-6}$alkyl or C$_{3-8}$cycloalkyl group], —N(R$^5$)CSN(R$^6$)(R$^7$) or —N(R$^5$)SO$_2$N(R$^6$)(R$^7$), provided that when t is zero and each of L$^3$ and L$^4$ is a covalent bond then u is the integer 1 and R$^4$ is other than a hydrogen atom.

When L$^3$ and/or L$^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^8$)— [where R$^8$ is a hydrogen atom or an optionally substituted straight or branched C$_{1-6}$alkyl group], —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— groups. Where the linker group contains two R$^8$ substituents, these may be the same or different.

When R$^{3a}$, R$^4$, R$^5$, R$^6$, R$^7$ and/or R$^8$ is present as a C$_{1-6}$alkyl group it may be a straight or branched C$_{1-6}$alkyl group, e.g. a C$_{1-3}$alkyl group such as a methyl, ethyl or i-propyl group. C$_{3-8}$cycloalkyl groups represented by R$^{3a}$, R$^4$, R$^5$, R$^6$ and/or R$^7$ include C$_{3-8}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an optionally substituted aliphatic or heteroaliphatic chain it may be any optionally substituted aliphatic or heteroaliphatic chain as described hereinafter for $Alk^1$.

Halogen atoms represented by $R^4$ in the optional $Ar^1$ substituents include fluorine, chlorine, bromine, or iodine atoms.

Examples of the substituents represented by -$L^3$(Alk$^1$)$_t$L$^4$(R$^4$)$_u$ when present in $Ar^1$ groups in compounds of the invention include atoms or groups -$L^3$Alk$^2$L$^4$R$^4$, -$L^3$Alk$^2$R$^4$, -$L^3$R$^4$, -R$^4$ and -Alk$^2$R$^4$ wherein $L^3$, Alk$^2$, $L^4$ and $R^4$ are as defined above. Particular examples of such substituents include -$L^3$CH$_2$L$^4$R$^4$, -$L^3$CH(CH$_3$)L$^4$R$^4$, -$L^3$CH(CH$_2$)$_2$L$^4$R$^4$, -$L^3$CH$_2$R$^4$, -$L^3$CH(CH$_3$)R$^4$, -$L^3$(CH$_2$)$_2$R$^4$, —CH$_2$R$^4$, —CH(CH$_3$)R$^4$, —(CH$_2$)$_2$R$^4$ and —R$^4$ groups.

Thus $Ar^1$ in compounds of the invention may be optionally substituted for example by one, two, three or more halogen atoms, e.g. fluorine, chlorine, bromine or iodine atoms, and/or $C_{1-6}$alkyl, e.g. methyl, ethyl, n-propyl, i-propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo $C_{1-6}$alkyl, e.g. —CF$_3$, —CHF$_2$, CH$_2$F, halo$C_{1-6}$alkoxy, e.g. —OCF$_3$, —OCHF$_2$, —OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$ dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$R$^5$ e.g. —CO$_2$CH$_3$ or —CO$_2$C(CH$_3$)$_3$, $C_{1-6}$ alkanoyl e.g. acetyl, thiol (—SH), thio$C_{1-6}$alkyl, e.g. thiomethyl or thioethyl, sulphonyl (—SO$_3$H), —SO$_3$Alk$^3$, $C_{1-6}$alkylsulphinyl, e.g. methylsulphinyl, $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkyl-aminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbo-nylamino or diethylaminocarbonylamino, $C_{1-6}$alkylaminocarbonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl; $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker -(Alk$^3$)$_d$L$^{2a}$-, where Alk$^3$ is an optionally substituted aliphatic or heteroaliphatic chain which may be any such chain as described hereinafter for Alk$^1$, d is zero or the integer 1 and $L^{2a}$ is a covalent bond or a linker atom or group as described hereinbefore for $L^3$.

Optionally substituted bicyclic heteroarylene groups represented by $Ar^2$ when present as part of the group $R^1$ include for example optionally substituted bicyclic $C_{5-9}$heteroaromatic groups containing for example one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen.

Particular examples of bicyclic heteroarylene groups include benzofurandiyl [2,3]-dihydrobenzofurandiyl, benzothiophenediyl, [2,3-dihydrobenzothiophenediyl, benzotriaxolediyl, indolediyl, iso-indolediyl, indazolediyl, benzimidazoladiyl, imidazo[1,2-a]-pyridinediyl, benzothiazolediyl, benzoxazolediyl, benzinoxazolediyl, benzopyranidiyl, [3,4-dihydro]benzopyrandiyl, quinazolinidiyl, quinoxalindiyl, naphthydrinediyl, e.g. 2,6-naphthyrinidinediyl or 2,7-naphthyridinediyl, cinnolinediyl, phthalazinediyl, pyrido[3,4-b]pyridinediyl, pyrido[3,2-b]pyridinediyl, pyrido[4,3-b]pyridinediyl, quinolinediyl, isoquinolinediyl, 5,6,7,8-tetrahydroquinolinidiyl, 5,6,7,8-tetrahydroisoquinolinidiyl, indolinediyl, azaindolinediyl, e.g. 4-, 5-, 6- or 7-azaindolinediyl, 1,2,3,4-tetrahydroquinolinediyl, 1,2,3,4-tetrahydro-1,8-naphthyridinediyl, 1,2,3,4-tetrahydro-1,7-naphthyridinediyl, 1,2,3,4-tetrahydro-1,6-naphthyridinediyl or 1,2,3, 4-tetrahydro-1,5-naphthyridineinyl groups.

Each divalent bicyclic or heteroarylene group represented by $Ar^2$ may be attached to the remainder of the molecule through any available ring carbon or nitrogen atoms.

The bicyclic heteroarylene groups represented by $Ar^2$ may be optionally substituted on any carbon or, when available nitrogen atom by one, two or more substituents selected from the atoms or groups -$L^3$(Alk$^2$)$_t$L$^4$(R$^4$)$_u$ described herein. Where two of these atoms or groups are present they may be the same or different.

When the group R is present in $R^1$ in compounds of the invention as a derivative of a carboxylic acid it may be for example a carboxylic acid ester or amide. Particular esters and amides include —$CO_2Alk^7$ and —$CONR^5R^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—$CO_2Alk^7$) and amide (—$CONR^5R^6$) derivatives of the carboxylic acid group (—$CO_2H$) in compounds of formula (1) may advantageously be used as prodrugs of the active compound. Such prodrugs are compounds which undergo biotransformation to the corresponding carboxylic acid prior to exhibiting their pharmacological effects and the invention particularly extends to produgs of the acids of formula (1). Such prodrugs are well known in the art, see for example International Patent Application No. WO00/23419, Bodor, N. (Alfred Benzon Symposium, 1982, 17, 156-177), Singh, G. et al (J. Sci. Ind. Res., 1996, 55, 497-510) and Bundgaard, H., (Design of Prodrugs, 1985, Elsevier, Amsterdam).

Esterified carboxyl groups represented by the group —$CO_2Alk^7$ include groups wherein $Alk^7$ is a straight or branched optionally substituted $C_{1-8}$alkyl group such as a methyl, ethyl, n-propyl, i-propyl, n-butyl, i-butyl, s-butyl or t-butyl group; an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$cycloalkyl$C_{1-8}$alkyl group such as a cyclopentylmethyl, cyclohexylmethyl or cyclohexylethyl group; an optionally substituted $C_{3-8}$heterocycloalkyl$C_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthio$C_{1-6}$alkyl group such as a cyclopentylthiomethyl group; an optionally substituted $C_{3-8}$cycloalkylsulfinyl$C_{1-6}$alkyl group such as a cyclopentylsulfinylmethyl group; an optionally substituted $C_{3-8}$cycloalkylsulfonyl$C_{1-6}$alkyl group such as a cyclopentylsulfonylmethyl group; an optionally substituted $C_{1-6}$alkyloxycarbonyl$C_{1-6}$alkyl group such as isobutoxycarbonylpropyl group; an optionally substituted $C_{1-6}$alkyloxycarbonyl$C_{1-6}$alkenyl group such as isobutoxycarbonylpentenyl group; an optionally substituted $C_{1-6}$alkyloxycarbonyloxy$C_{1-6}$alkyl group such as an isopropoxycarbonyloxyethyl e.g. a 1-(isopropoxycarbonyloxy)ethyl, 2-(isopropoxycarbonyloxy)ethyl or ethyloxycarbonyloxymethyl group; an optionally substituted $C_{1-6}$alkyloxycarbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N-$C_{6-12}$aryl-N-$C_{1-6}$alkylamino$C_{1-6}$alkyl group such as a N-phenyl-N-methylaminomethyl group; an optionally substituted N-di-$C_{1-8}$alkyl-carbamoyl$C_{1-8}$alkyl group such as a N-diethylcarbamoylmethyl group; an optionally substituted $C_{6-10}$aryl$C_{1-6}$alkyl group such as an optionally substituted benzyl, phenylethyl, phenylpropyl, 1-naphthylmethyl or 2-naphthylmethyl group; a $C_{6-10}$aryl group such as an optionally substituted phenyl, 1-naphthyl or 2-naphthyl group; a $C_{6-10}$aryloxy$C_{1-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl; a $C_{6-12}$arylsulfinyl$C_{1-8}$alkyl group such as an optionally substituted phenylsulfinylmethyl group; a $C_{6-12}$arylsulfonyl$C_{1-8}$alkyl group such as an optionally substituted phenylsulfonylmethyl group; an optionally substituted $C_{1-8}$alkanoyloxy$C_{1-8}$alkyl group, such as a acetoxymethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substigtuted triglyceride e.g. a 1,3-di-$C_{1-8}$alkylglycerol-2-yl group such as a 1,3-diheptylglycerol-2-yl group. Optional substituents present on the $Alk^7$ group include $R^{13a}$ substituents described below.

It will be appreciated that in the forgoing list of $Alk^7$ groups the point of attachment to the remainder of the compound of formula (1) is via the last described part of the $Alk^7$ group. Thus, for example a methoxyethyl group would be attached by the ethyl group, whilst a morpholinyl-N-ethyl group would be attached via the N-ethyl group.

It will be further appreciated that in the forgoing list of $Alk^7$ groups, where not specifically mentioned, alkyl groups may be replaced by alkenyl or alkynyl groups where such groups are as previously defined for $Alk^1$. Additionally these alkyl, alkenyl or alkynyl groups may optionally be interrupted by one, two or three linker atoms or groups where such linker atoms and groups are as previously defined for $L^3$.

When the group $R^2$ is present in compounds of the invention as a $C_{1-6}$alkyl group it may be for example a straight or branched $C_{1-6}$alkyl group e.g. a $C_{1-3}$alkyl group such as a methyl or ethyl group.

When present in the group $R^x$, $R^y$ and/or $R^z$ in compounds of formula (1) the linker atom or group represented by $L^1$ may be any linker atom or group as described above for the linker atom or group $L^3$. In addition $L^1$ may also be a —Se— atom.

When $Alk^1$ is present in the group $R^x$, $R^y$ and/or $R^z$ in compounds of formula (1) as an optionally substituted aliphatic chain it may be an optionally substituted $C_{1-10}$aliphatic chain. Particular examples include optionally substituted straight or branched chain $C_{1-6}$alkylene, $C_{2-6}$alkenylene, or $C_{2-6}$alkynylene chains.

Particular examples of aliphatic chains represented by $Alk^1$ include optionally substituted —$CH_2$—, —$(CH_2)_2$—, —$CH(CH_3)CH_2$—, —$(CH_2)_2CH_2$—, —$(CH_2)_3CH_2$—, —$CH(CH_3)(CH_2)_2$—, —$CH_2CH(CH_3)CH_2$—, —$C(CH_3)_2CH_2$—, —$CH_2C(CH_3)_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —$CH_2$CHCH—, —CHCHCH$_2$CH$_2$—, —$CH_2$CHCHCH$_2$—, —$(CH_2)_2$CHCH—, —CC—, —CCCH$_2$—, —$CH_2$CC—, —CCCH$_2$CH$_2$—, —$CH_2$CCCH$_2$— or —$(CH_2)_2$CCH— groups.

Heteroaliphatic chains represented by $Alk^1$ when present in the group $R^x$, $R^y$ and/or $R^z$ in compounds of formula (1) include the aliphatic chains just described for $Alk^1$ but with each additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic chain, or may be positioned at its terminal carbon atom to connect the chain to an adjoining atom or group. Particular examples include optionally substituted —$CH_2L^5$—, —$CH_2CH_2L^5$—, -$L^5CH_2$—, -$L^5CH_2CH_2$—, —$CH_2L^5CH_2CH_2$—, —$(CH_2)_2L^5CH_2$—, —$(CH_2)_3L^5CH_2$—, -$L^5(CH_2)_3$, —$CH_2L^5CH_2CHL^5CH_2$— and —$(CH_2)_2L^5CH_2CH_2$— chains.

The optional substituents which may be present on aliphatic or heteroaliphatic chains represented by $Alk^1$ include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group as defined above for $R^4$, —$CONHR^9$, —$CON(R^9)_2$, —$COCH_3$, $C_{1-6}$alkoxy, e.g. methoxy or ethoxy, thiol, —$S(O)R^9$, —$S(O)_2R^9$, $C_{1-6}$alkylthio e.g. methylthio or ethylthio, amino or substituted amino groups. Substituted amino groups include —$NHR^9$ and —$N(R^9)_2$ groups. Where two $R^9$ groups are present in any of the above substituents these may be the same or different.

Optionally substituted cycloaliphatic groups represented by the group $R^3$ when present in the group, $R^x$, $R^y$ and/or $R^z$ in compounds of the invention include optionally substituted $C_{3-10}$cycloaliphatic groups. Particular examples include optionally substituted $C_{3-10}$cycloalkyl, e.g. $C_{3-7}$cycloalkyl or $C_{3-10}$cycloalkenyl, e.g $C_{3-7}$cycloalkenyl groups.

Optionally substituted heterocycloaliphatic groups represented by the group $R^3$ when present in the group $R^x$, $R^y$ and/or $R^z$ include optionally substituted $C_{3-10}$heterocycloaliphatic groups. Particular examples include optionally substituted $C_{3-10}$heterocycloalkyl, e.g. $C_{3-7}$heterocycloalkyl, or $C_{3-10}$heterocycloalkenyl, e.g. $C_{3-7}$hetercycloalkenyl groups, each of said groups containing one, two, three or four heteroatoms or heteroatom-containing groups $L^5$ as defined above in place of ring carbon atoms.

Optionally substituted polycycloaliphatic groups represented by the group $R^3$ when present in the group $R^x$, $R^y$ and/or $R^z$ include optionally substituted $C_{7-10}$bi- or tricycloalkyl or $C_{7-10}$bi- or tricycloalkenyl groups. Optionally substituted heteropolycycloaliphatic groups represented by the group $R^3$ include the optionally substituted polycycloalkyl groups just described, but with each group containing one, two, three or four $L^5$ atoms or groups in place of ring carbon atoms.

Particular examples of cycloaliphatic, polycycloaliphatic, heterocycloaliphatic and heteropolycycloaliphatic groups represented by the group $R^3$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, tetrahydrothiophenyl, tetrahydrothiophene-1-oxide, tetrahydrothiophene-1,1-dioxide, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, tetrahydropyranyl, tetrahydrothiopyranyl, tetrahydrothiopyran-1-oxide, tetrahydrothiopyran-1,1-dioxide, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group $R^3$ include one, two, three or more substituents each selected from halogen atoms, e.g. fluorine, chlorine, bromine or iodine atoms, or $C_{1-6}$alkyl, e.g. methyl, ethyl, propyl or i-propyl, halo$C_{1-6}$alkyl, e.g. halomethyl or haloethyl such as difluoromethyl or trifluoromethyl, optionally substituted by hydroxyl, e.g. —$C(OH)(CF_3)_2$, $C_{1-6}$alkoxy, e.g. methoxy, ethoxy or propoxy, halo$C_{1-6}$alkoxy, e.g. halomethoxy or haloethoxy such as difluoromethoxy or trifluoromethoxy, thiol, $C_{1-6}$alkylthio e.g. methylthio, ethylthio or propylthio, or —$(Alk^4)_gR^{10}$ groups in which $Alk^4$ is a straight or branched $C_{1-3}$alkylene chain, g is zero or the integer 1 and $R^{10}$ is a —OH, —SH, —$N(R^{11})_2$, (in which $R^{11}$ is an atom or group as defined herein for $R^7$), —CN, —$CO_2R^{11}$, —$NO_2$, —$CON(R^{11})_2$, —$CSN(R^{11})_2$, —$COR^{11}$, —$CSN(R^{11})_2$, —$N(R^{11})COR^{11}$, —$N(R^{11})CSR^{11}$, —$SO_2N(R^{11})_2$, —$N(R^{11})SO_2R^{11}$, —$N(R^{11})CON(R^{11})_2$, —$N(R^{11})CSN(R^{11})$, $N(R^{11})SO_2N(R^{11})_2$ or optionally substituted phenyl group. Where two $R^{11}$ atoms or groups are present in these substituents these may be the same or different or joined to form a heterocyclic ring as previously described when $R^5$ and $R^6$ are joined together. Optionally substituted phenyl groups include phenyl substituted by one, two or three of the $R^{13}$ groups described below.

Additionally, when the group $R^3$ is a heterocycloaliphatic group containing one or more nitrogen atoms each nitrogen atom may be optionally substituted by a group -$(L^6)_p(Alk^5)_qR^{12}$ in which $L^6$ is —C(O)—, —C(O)O—, —C(S)—, —$S(O)_2$—, —$CON(R^8)$-[where $R^8$ is as previously defined], —$CSN(R^8)$— or —$SO_2N(R^8)$—; p is zero or an integer 1; $Alk^5$ is an optionally substituted aliphatic or heteroaliphatic chain; q is zero or an integer 1; and $R^{12}$ is a hydrogen atom or an optionally substituted cycloaliphatic, heterocycloaliphatic, polycyploaliphatic, polyheterocycloaliphatic, aromatic or heteroaromatic group.

$C_{1-3}$alkylene chains represented by $Alk^4$ include —$CH_2$—, —$CH_2CH_2$—, —$CH_2CH_2CH_2$—, —$CH(CH_3)CH_2$— and —$CH_2CH(CH_3)$— chains.

Optionally substituted aliphatic or heteroaliphatic chains represented by $Alk^5$ include those optionally substituted chains described above for $Alk^1$. Optional substituents which may be present on these groups include those described above in relation to $Alk^1$.

Cycloaliphatic, heterocycloaliphatic, polycycloaliphatic or polyheterocycloaliphatic groups represented by $R^{12}$ include those groups just described for the group $R^3$. Optional substituents which may be present on those groups include those described above in relation to $R^3$ cycloaliphatic groups.

Aromatic or heteroaromatic groups represented by $R^{12}$ include those groups described herein for the group $Ar^1$. Optional substituents which may be present on these groups include those $R^{13}$ optional substituents described hereinafter.

When the group $R^3$ is an optionally substituted aromatic or heteroaromatic group it may be for example an aromatic or heteroaromatic group as described herein for the group $Ar^1$.

Optional substituents which may be present on the aromatic or heteroaromatic groups represented by the group $R^3$ include one, two, three or more substituents, each selected from an atom or group $R^{13}$ in which $R^{13}$ is —$R^{13a}$ or -$Alk^6(R^{13a})_m$, where $R^{13a}$ is a halogen atom, or an amino (—$NH_2$), substituted amino, nitro, cyano, amidino, hydroxyl (—OH), substituted hydroxyl, formyl, carboxyl (—$CO_2H$), esterified carboxyl, thiol (—SH), substituted thiol, —$COR^{14}$ [where $R^{14}$ is an -$Alk^6(R^{13a})_m$, aryl or heteroaryl group], —$CSR^{14}$, —$SO_3H$, —$SOR^{14}$, —$SO_2R^{14}$, —$SO_3R^{14}$, —$SO_2NH_2$, —$SO_2NHR^{14}$, $SO_2N(R^{14})_2$, —$CONH_2$, —$CSNH_2$, —CONHR$^{14}$, —CSNHR$^{14}$, —CON[R$^{14}$]$_2$, —CSN(R$^{14}$)$_2$, —N(R$^{11}$)SO$_2$R$^{14}$, —N(SO$_2$R$^{14}$)$_2$, —NH(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where —NHet$^1$ is an optionally substituted C$_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$) Het$^2$ [where Het$^2$ is an optionally substituted monocyclic C$_{5-7}$carbocyclic group optionally containing one or more —O— or —S— atoms or —N(R$^{11}$), —C(O)— or —C(S)— groups], -Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, aryl or heteroaryl group; Alk$^6$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N(R$^{15}$)— groups [where R$^{15}$ is a hydrogen atom or C$_{1-6}$alkyl, e.g. methyl or ethyl group]; and m is zero or an integer 1, 2 or 3. It will be appreciated that when two R$^{11}$ or R$^{14}$ groups are present in one of the above substituents, the R$^{11}$ or R$^{14}$ groups may be the same or different.

When in the group -Alk$^6$(R$^{13a}$)$_m$ m is an integer 1, 2 or 3, it is to be understood that the substituent or substituents R$^{13a}$ may be present on any suitable carbon atom in -Alk$^6$. Where more than one R$^{13a}$ substituent is present these may be the same or different and may be present on the same or different atom in -Alk$^6$. Clearly, when m is zero and no substituent R$^{13a}$ is present the alkylene, alkenylene or alkynylene chain represented by Alk$^6$ becomes an alkyl, alkenyl or alkynyl group.

When R$^{13a}$ is a substituted amino group it may be for example a group —NHR$^{14}$ [where R$^{14}$ is as defined above] or a group —N(R$^{14}$)$_2$ wherein each R$^{14}$ group is the same or different.

When R$^{13a}$ is a halogen atom it may be for example a fluorine, chlorine, bromine, or iodine atom.

When R$^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group R$^{13a}$ include groups of formula —CO$_2$Alk$^8$ wherein Alk$^8$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^8$ group include R$^{13a}$ substituents described above.

When Alk$^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^8$)— groups.

Aryl or heteroaryl groups represented by the groups R$^{13a}$ or R$^{14}$ include mono- or bicyclic optionally substituted C$_{6-12}$aromatic or C$_{1-9}$ heteroaromatic groups as described above for the group Ar$^1$. The aromatic and heteroaromatic groups may be attached to the remainder of the compound of formula (1) by any carbon or hetero e.g. nitrogen atom as appropriate.

When —NHet$^1$ or -Het$^2$ forms part of a substituent R$^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or -Het$^2$ include those optional substituents described above in relation to aliphatic chains represented by Alk$^1$.

Particularly useful atoms or groups represented by R$^{13}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{4-7}$cycloalkyl, e.g. cyclobutyl, cyclopentyl, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino, ethylamino or propylamino, C$_{6-12}$arylC$_{1-6}$alkylamino, e.g. benzylamino, 4-fluorobenzylamino or 4-hydroxyphenylethylamino, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkylamino, e.g. aminoethylamino or aminopropylamino, optionally substituted Het$^1$NC$_{1-6}$alkylamino, e.g. 3-morpholinopropylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, hydroxyC$_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^7$ [where Alk$^7$ is as defined above], C$_{1-6}$ alkanoyl e.g. acetyl, propyryl or butyryl, optionally substituted benzoyl, thiol (—SH), thioC$_{1-6}$alkyl, e.g. thiomethyl or thioethyl, —SC(=NH)NH$_2$, sulphonyl (—SO$_3$H), —SO$_3$Alk$^7$, C$_{1-6}$alkylsulphinyl, e.g. methylsuphinyl, ethylsulphinyl or propylsulphinyl, C$_{1-6}$alkylsulphonyl, e.g. methylsulphonyl, ethylsulphonyl or propylsulphonyl, aminosulphonyl (—SO$_2$NH$_2$), C$_{1-6}$alkylaminosulphonyl, e.g. methylaminosulphonyl, ethylaminosulphonyl or propylaminosulphonyl C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$alkylaminoC$_{1-6}$alkylaminocarbonyl, e.g. methylaminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, halo$C_{1-6}$alkylsulphonylamino, e.g. trifluoromethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino; optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^3$.

When the groups $R^x$ and $R^y$ are joined together to form an optionally substituted spiro linked cycloaliphatic or heterocycloaliphatic group joined to the cyclobutenone ring as defined by formula (1) it may be any such cycloaliphatic or heterocycloaliphatic group as previously described for $R^3$. Optional substituents which may be present on such spiro linked cycloaliphatic or heteroaliphatic groups include those optional substituents as described in relation to $R^3$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $R^1$ is preferably an $Ar^1L^2Ar^2Alk$- group. In compounds of this type $Ar^1$ is preferably an optionally substituted phenyl, monocyclic heteroaromatic or bicyclic heteroarbmatic group. Particularly useful monocyclic heteroaromatic groups are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these $Ar^1$ groups include halogen atoms or alkyl, haloalkyl, —OR$^5$, —SR$^5$, —NR$^5$R$^6$, —CO$_2$H, —CO$_2$CH$_3$, —NO$_2$, —N(R$^5$)COR$^6$ or —CN groups as described above in relation to the compounds of formula (1). Particularly useful bicyclic heteroaromatic groups represented by $Ar^1$ include optionally substituted ten-membered fused-ring heteroaromatic groups containing one or two heteroatoms, especially nitrogen atoms. Particular examples include optionally substituted naphthyridinyl, especially 2,6-naphthyridinyl, 2,7-naphthyridinyl, quinolinyl and isoquinolinyl, especially isoquinolin-1-yl groups. Particularly useful optional substituents include those described hereinafter.

In the compounds according to the invention X is preferably an —N(R$^2$)— group.

In the compounds according to the invention $Ar^2$ is preferably an optionally substituted indolediyl or indolinediyl group.

In the compounds according to the invention f is preferably the integer 1 or 2.

A particularly useful group of compounds according to the invention has the formula (2a):

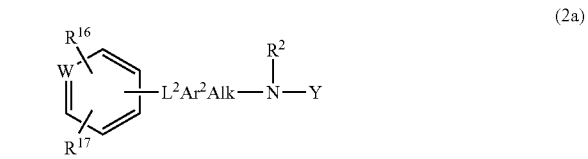

(2a)

wherein —W= is —CH= or —N=;

$R^{16}$ and $R^{17}$, which may be the same or different is each a hydrogen atom or an atom or group -L$^3$(Alk$^2$)$_t$L$^4$(R$^4$)$_u$ in which L$^3$, Alk$^2$, t, L$^4$, R$^4$ and u are as defined previously;

Y is a group of formula

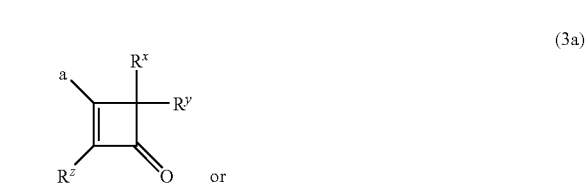

(3a)

or

-continued

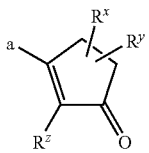
(3b)

where a indicates the point of attachment of the group —N(R²)—;

L², Ar², Alk, R², Rˣ, Rʸ and Rᶻ are as defined for formula (1);

and the salts, solvates, hydrates and N-oxides thereof.

—W═ in compounds of formula (2a) is preferably —C═, —N═ or —N(O)═. Most preferably W is —N═.

In one preferred class of compounds of formula (2a) L² is located in the para position relative to W.

R¹⁶ and R¹⁷ when present as a substituent other than a hydrogen atom in compounds of formula (2a) is each preferably as particularly described above for compounds of formula (1). Particularly useful R¹⁶ and R¹⁷ substituents when present include halogen atoms, especially fluorine or chlorine atoms, or $C_{1-6}$alkyl, especially methyl, ethyl or isopropyl, halo$C_{1-6}$alkyl especially halomethyl, most especially —CF₃, —CHF₂ or —CH₂F, $C_{1-6}$alkoxy especially methoxy or halo$C_{1-6}$alkoxy especially halomethoxy, most especially —OCF₃, —OCHF₂ or —OCH₂F groups.

A further particularly useful group of compounds according to the invention has the formula (2b):

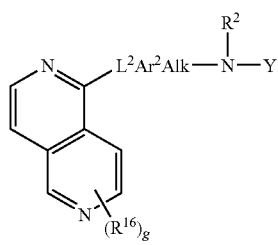
(2b)

wherein g is the integer 1, 2, 3 or 4;

each R¹⁶ is an atom or group -L³(Alk²)$_t$L⁴(R⁴)$_u$ in which L³, Alk², t, L⁴, R⁴ and u are as defined previously;

Y is a group of formula (3a) or (3b);

L², Ar², Alk, R², Rˣ, Rʸ and Rᶻ are as defined for formula (1);

and the salts, solvates, hydrates and N-oxides thereof.

Particularly useful R¹⁶ substituents when present in compounds of formula (2b) include halogen atoms, especially fluorine, chlorine or bromine atoms, or $C_{1-6}$alkyl e.g. methyl, ethyl or isopropyl, halo$C_{1-6}$alkyl, especially halomethyl, most especially —CF₃, $C_{1-6}$alkoxyl, especially methoxy, halo$C_{1-6}$alkoxy, especially halomethoxy, most especially —OCF₃, —CN, —CO₂CH₃, —NO₂, amino (—NH₂), substituted amino (—NR⁵R⁶) especially —NHCH₃ and —N(CH₃)₂, —N(R⁵)COCH₃, especially —NHCOCH₃ groups or optionally substituted phenyl, furyl, thienyl, imidazolyl, pyridyl and pyrimidinyl groups.

A further particularly useful group of compounds according to the invention has the formula (2c):

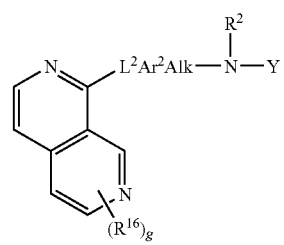
(2c)

wherein Y, R¹⁶, g, L², Ar², Alk, R², Rˣ, Rʸ and Rᶻ are as defined for formula (2b);

and the salts, solvates, hydrates and N-oxides thereof.

Each R¹⁶ atom or group in compounds of formula (2c) may be independently selected from an atom or group -L³(Alk²)$_n$L⁴(R⁴)$_u$ as previously particularly defined for compounds of formula (2b).

A further particularly useful group of compounds according to the invention has the formula (2d):

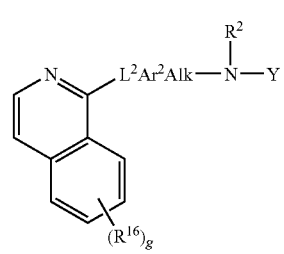
(2d)

wherein R¹⁶, g, L², Ar², Alk, R²¹, Rˣ, Rʸ and Rᶻ are as defined for formula (2b):

and the salts, solvates, hydrates and N-oxides thereof.

Each R¹⁶ atom or group in compounds of formula (2d) may be independently selected from an atom or group -L³(Alk²)$_t$L⁴(R⁴)$_u$ as previously defined for compounds of formula (2b).

In one preferred class of compounds of formula (2d) at least one R¹⁶ atom or group is present at the 3-position of the isoquinoline ring. In a preferred group of compounds of this class R¹⁶ is an optionally substituted phenyl ring where the preferred optional substituents are those atoms or groups as defined for R¹⁶.

It will be understood that compounds according to formulae (2a), (2b), (2c) and (2d) include, where applicable, the corresponding hydroxy tautomers.

Alk in compounds of the invention is preferably —CH (CH₂R)— or, especially, —CH₂CH(R)—.

In one preferred class of compounds of formulae (1), (2a), (2b), (2c) and (2d) R is a —CO₂H group.

In another preferred class of compounds of formulae (1) and (2) R is an esterified carboxyl group of formula —CO₂Alk⁷. In this class of compound Alk⁷ is preferably a $C_{1-8}$alkyl group, especially a methyl, ethyl, propyl, i-propyl, butyl, t-butyl or pentyl group, an optionally substituted $C_{3-8}$cycloalkyl group, especially a cyclopropyl, cyclobutyl, cyclopentyl, cyclohexyl or cycloheptyl group, an optionally substituted $C_{6-10}$aryl group, especially a phenyl group, an optionally substituted $C_{6-10}$aryl$C_{1-6}$alkyl group, especially a benzyl group, an optionally substituted $C_{3-8}$heterocycloalkyl$C_{1-6}$alkyl group, especially a morpholinyl-N-ethyl group, an optionally substituted N-di-$C_{1-8}$alkylamino$C_{1-8}$alkyl group, especially a N-dimethylaminoethyl or N-diethylaminoethyl group or an optionally substituted $C_{1-6}$alkyloxy$C_{1-6}$alkyl group, especially a methyloxyethyl group. Especially preferred esterified carboxyl groups include —$CO_2CH_3$, —$CO_2CH_2CH_3$, —$CO_2CH_2CH_2CH_3$, —$CO_2CH(CH_3)_2$ and —$CO_2C(CH_3)_3$ groups.

In general in compounds of formula (1) when X is a —$N(R^2)$ group and in compounds of formulae (2a), (2b), (2c) and (2d) $R^2$ is preferably a hydrogen atom.

The group $Ar^2$ in compounds of formulae (1), (2a), (2b), (2c) and (2d) is preferably an optionally substituted indolediyl or indolinediyl group, especially a 1,4-indolediyl, 1,5-indolediyl 1,4-indolinediyl or 1,5-indolinediyl group of formula:

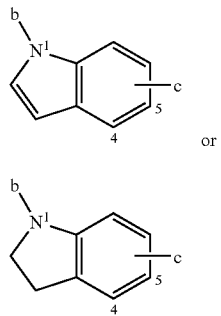

where b indicates the point of attachment of the group $L^2$ and c indicates the point of attachment of the group Alk.

Most preferably $Ar^2$ is an optionally substituted 1,5-indolediyl or 1,5-indolinediyl group, especially preferred being a 1,5-indolinediyl group.

Particularly preferred optional substituents which may be present on $Ar^2$ in compounds of the invention include halogen atoms, especially fluorine, chlorine or bromine atoms, or $C_{1-6}$alkyl e.g. methyl, ethyl or i-propyl, halo$C_{1-6}$alkyl especially halomethyl, most especially —$CF_3$, $C_{1-6}$alkoxy especially methoxy or halo$C_{1-6}$alkoxy, especially halomethoxy, most especially —$OCF_3$, —CN, —$CO_2CH_3$, —$NO_2$, amino (—$NH_2$), substituted amino ($NR^5R^6$) especially —$NHCH_3$ and —$N(CH_3)_2$ and —$N(R^5)COCH_3$, especially —NHCOCH_3 groups.

In compounds of formula (2a) $L^2$ is preferably -$(Alk^3)_d$$L^{2a}$-, where d is the integer 1, $Alk^3$ is preferably a —$CH_2$— chain and $L^{2a}$ is a covalent bond or -$(Alk^3)_d$$L^{2a}$- where d is zero and $L^{2a}$ is a —$C(O)$— or —$C(S)$— group, most preferably a —$C(O)$— group. In compounds of formula (2a) $L^2$ is most preferably -$(Alk^3)_d$$L^{2a}$- where d is zero and $L^{2a}$ is a —CO— group In general in compounds of formulae (2b), (2c) and (2d) $L^2$ is preferably a covalent band.

In one generally preferred class of compounds of formulae (1), (2a), (2b), (2c) and (2d) where Y is a group of formula (3a) $R^x$, $R^y$ and/or $R^z$ is an optionally substituted alkyl group, most preferably an optionally substituted $C_{1-8}$alkyl group such as a methyl, ethyl, n-propyl, i-propyl, n-butyl, n-heptyl, or n-hexyl group. Particularly preferred optional substituents which may be present on such $R^x$, $R^y$ and/or $R^z$ alkyl groups include halogen atoms, especially fluorine or chlorine atoms, $C_{1-6}$alkoxy groups, especially methoxy, halo$C_{1-6}$alkoxy groups, especially —$OCF_3$, —CN, —$CO_2CH_3$, —$NO_2$, substituted amino (—$NR^5R^6$) especially —$NHCH_3$ and —$N(CH_3)_2$ and optionally substituted phenyl groups where the optional substituents are as defined for $R^{16}$.

In a preferred class of compounds of formulae (1), (2a), (2b), (2c) and (2d) in which Y is a group of formula (3a) $R^z$ is a hydrogen atom.

In another preferred class of compounds of formulae (1), (2a), (2b), (2c) and (2d) in which Y is a group of formula (3a) $R^x$ is a hydrogen atom.

In another preferred class of compounds of formulae (1), (2a), (2b), (2c) and (2d) in which Y is a group of formula (3a) $R^x$ and $R^y$ is each a hydrogen atom.

In another preferred class of compounds of formulae (1), (2a), (2b), (2c) and (2d) in which Y is a group of formula (3a) $R^z$ is a halogen atom, especially a fluorine, chlorine, bromine or iodine atom, most especially a chlorine or bromine atom.

In another preferred class of compounds of formulae (1), (2a), (2b), (2c) and (2d) in which Y is a group of formula (3a) $R^z$ is a group -$L^1(Alk^1)_nR^3$. In this class of compounds $L^1$ is preferably an —O—, —S— or or —Se— atom or —$N(R^8)$—, especially —NH— or —$N(CH_3)$— group. Most preferably $L^1$ is a —S— atom. $R^3$ is preferably a hydrogen atom or an optionally substituted $C_{3-10}$heterocycloaliphatic, especially $C_{3-7}$heterocycloalkyl group, most especially an optionally substituted piperidinyl, hexahydropyridinyl, piperazinyl, pyrrolidinyl, imidazolidinyl or pyrazolidinyl group, or an optionally substituted $C_{6-12}$aromatic group, most preferably an optionally substituted phenyl group or an optionally substituted $C_{1-9}$heteroaromatic group, preferably an optionally substituted monocyclic $C_{1-9}$heteroaromatic group, most preferably a 5- or 6-membered monocyclic heteroaromatic group containing one, two or three heteroatoms selected from oxygen, sulphur or nitrogen atoms, especially an optionally substituted furyl, thienyl, pyridyl or pyrimidinyl group. Optional substituents which may be present on such heterocycloaliphatic groups include those substituents as described hereinafter when $R^x$ and $R^y$ are joined to form an optionally substituted spiro linked heterocycloaliphatic group. Optional substituents which may be present on such aromatic and heteroaromatic groups include those $R^{16}$ substituents as described hereinbefore in relation to compounds of formula (2a). In one preferred group of compounds of this class n is zero. In another preferred group of compounds of this class $L^1$ is a covalent bond and n is zero. In a further preferred group of compounds of this class n is the integer 1 and $Alk^1$ is preferable an optionally substituted aliphatic chain, most preferably an optionally substituted $C_{1-6}$alkylene chain, especially a —$CH_2$—, —$CH_2CH_2$— or —$CH_2CH(CH_3)$ chain.

In another preferred class of compounds of formulae (1), (2a), (2b), (2c) and (2d) in which Y is a group of formula (3a) $R^x$ and $R^z$ is each a hydrogen atom.

In another preferred class of compounds of formulae (1), (2a), (2b), (2c) and (2d) in which Y is a group of formula (3a) $R^x$ is a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred class of compounds of formulae (1), (2a), (2b), (2c) and (2d) in which Y is a group of formula (3a) $R^x$ and $R^y$ is each a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred class of compounds of formulae (1), (2a), (2b), (2c) and (2d) in which Y is a group of formula (3a) $R^x$ is a hydrogen atom and $R^y$ is an optionally substituted alkyl group as just described for generally preferred alkyl groups.

In another preferred class of compounds of formulae (1), (2a), (2b), (2c) and (2d) in which Y is a group of formula (3a) $R^x$ and $R^z$ is each a hydrogen atom and $R^y$ is an optionally substituted alkyl group as just described.

In another preferred class of compounds of formulae (1), (2a), (2b), (2c) and (2d) in which Y is a group of formula (3a) $R^x$ is a hydrogen atom, $R^z$ is a halogen atom, especially a fluorine, chlorine, bromine or iodine atom, most especially a chlorine or bromine atom or $R^z$ is a group $-L^1(Alk^1)_nR^3$, especially a group as just particularly described and $R^y$ is an optionally substituted alkyl group as just described for generally preferred alkyl groups.

In another preferred class of compounds of formulae (1), (2a), (2b), (2c) and (2d) in which Y is a group of formula (3a) $R^x$ is a hydrogen atom and $R^y$ and $R^z$ is each an optionally substituted alkyl group as just described for generally preferred alkyl groups.

In another preferred class of compounds of formulae (1), (2a), (2b), (2c) and (2d) in which Y is a group of formula (3a) $R^x$ and $R^y$ is each an optionally substituted alkyl group as just described for generally preferred alkyl groups.

In another preferred class of compounds of formulae (1), (2a), (2b), (2c) and (2d) in which Y is a group of formula (3a) $R^x$ and $R^y$ is each an optionally substituted alkyl group as just described for generally preferred alkyl groups and $R^z$ is a hydrogen atom.

In another preferred class of compounds of formulae (1), (2a), (2b), (2c) and (2d) in which Y is a group of formula (3a) $R^x$ and $R^y$ is each an optionally substituted alkyl group as just described for generally preferred alkyl groups and $R^z$ is a halogen atom, especially a fluorine, chlorine, bromine or iodine atom, most especially a chlorine or bromine atom, or $R^z$ is a group $-L^1(Alk^1)_nR^3$ as just described.

In another preferred class of compounds of formulae (1), (2a), (2b), (2c) and (2d) in which Y is a group of formula (3a) $R^x$, $R^y$ and $R^z$ is each an optionally substituted alkyl group as just described for generally preferred alkyl groups.

In another preferred class of compounds of formulae (1), (2a), (2b), (2c) and (2d) in which Y is a group of formula (3a) $R^x$ and $R^y$ are joined to form an optionally substituted spiro linked cycloaliphatic group particularly a $C_{3-10}$cycloaliphatic group, most particularly a $C_{3-8}$cycloalkyl group, especially an optionally substituted cyclopentyl cyclohexyl, cycloheptyl or cyclooctyl group. Particularly preferred optional substituents which may be present on such spiro linked cycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —$OCF_3$, —CN, —$CO_2CH_3$, —$NO_2$ and substituted amino (—$N(R^{11})_2$), especially —$NHCH_3$ and —$N(CH_3)_2$ groups. In a preferred group of compounds of this class $R^z$ is an alkyl group as just described. In a further preferred group of this class $R^z$ is a halogen atom, especially a fluorine, chlorine, bromine or iodine atom, most especially a chlorine or bromine atom. In a still further preferred group of this class $R^z$ is a group $-L^1(Alk^1)_nR^3$ as just described.

In another preferred class of compounds of formulae (1), (2a), (2b), (2c) and (2d) in which Y is a group of formula (3a) $R^x$ and $R^y$ are joined to form an optionally substituted spiro linked heterocycloaliphatic group, particularly an optionally substituted $C_{3-10}$heterocycloaliphatic group, most particularly an optionally substituted $C_{3-7}$heterocycloalkyl group, especially an optionally substituted $C_{3-7}$heterocycloalkyl group containing one or two —O—, —S—, —S(O)—, —S(O)$_2$—, —NH— or —C(O)— heteroatoms or heteroatom-containing groups. Especially preferred optionally substituted heterocycloaliphatic groups include optionally substituted 5-and 6-membered heterocycloalkyl groups containing one heteroatom or heteroatom-containing group as just described, especially optionally substituted pyrrolidinyl, tetrahydrofuranyl, tetrahydrothiophenyl, tetrahydrothiophene-1-oxide, tetrahydrothiophene-1,1-dioxide, piperidinyl, tetrahydropyranyl, tetrahydrothiopyranyl tetrahydrothiopyran-1-oxide or tetrahydrothiopyran-1,1-dioxide groups. Particularly preferred optional substituents which may be present on such spiro linked heterocycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —$OCF_3$, —CN, —$CO_2CH_3$, —$NO_2$ and substituted amino (—$N(R^{11})_2$), especially —$NHCH_3$ and —$N(CH_3)_2$ groups. In addition when the spiro linked heterocycloaliphatic group contains a nitrogen atom this may be substituted by a group $-(L^6)_p(Alk^5)_qR^{12}$ where $L^6$ is preferably —C(O)— or —S(O)$_2$—, $Alk^5$ is preferably an optionally substituted $C_{1-6}$alkylene chain, especially a —$CH_2$—, —$(CH_2)_2$— or —$CH(CH_3)CH_2$— chain or an optionally substituted hetero$C_{1-6}$alkylene chain, especially —$CH_2L^5$—, —$CH_2CH_2L^5$-, -$L^5CH_2$— or -$L^5CH_2CH_2$ chain where $L^5$ is an —O— or —S— atom or —NH or —N(CH$_3$)— group and $R^{12}$ is a hydrogen atom or an optionally substituted phenyl ring where preferred optional substituents include those atoms and groups as defined hereinbefore for $R^{16}$ in relation to formula (2b). In one preferred group of compounds of this class $R^z$ is a hydrogen atom. In another preferred group of compounds of this class $R^z$ is an alkyl group as just described. In a further preferred group of compounds of this class $R^z$ is a halogen atom, especially a fluorine, chlorine, bromine or iodine atom, most especially a chlorine or bromine atom. In a still further preferred group of compounds of this class $R^z$ is a group $-L^1(Alk^1)_nR^3$ as just described.

In another preferred class of compounds of formulae (1), (2a), (2b), (2c) and (2d) in which Y is a group of formula (3b) $R^z$ is preferably a hydrogen or halogen atom, especially a fluorine, chlorine or bromine atom or a nitro (—$NO_2$), $C_{1-6}$alkyl, especially —$CH_3$, —$CH_2CH_3$, —$CH_2CH_2CH_3$, —$(CH_2)_3CH_3$, —$CH(CH_3)_2$, —$C(CH_3)_3$, —$CH(CH_2CH_3)_2$, —$CH_2CH(CH_3)_2$ or —$CH_2C(CH_3)_3$, $C_{2-6}$alkenylene, especially —$CH_2CHCH_2$ or —$CH_2CH_2CHCH_2$, $C_{2-6}$alkynylene, especially —$CH_2CCH$ or —$CH_2CH_2CCH$, $C_{1-6}$alkyl $C_{6-12}$aromatic, especially optionally substituted benzyl or phenylethyl $C_{6-12}$aromatic, especially optionally substituted phenyl, optionally substituted $C_{3-10}$cycloaliphatic, especially optionally substituted $C_{3-7}$cycloalkyl, most especially optionally substituted cyclopentyl, cyclohexyl or cycloheptyl or optionally substituted $C_{3-10}$heterocycloaliphatic, especially $C_{3-7}$heterocycloalkyl, most especially tetrahydropyranyl or tetrahydrothiopyranyl groups. Particularly preferred optional substituents which may be present on such groups include halogen atoms, especially fluorine or chlorine atoms, $C_{1-6}$alkoxy groups, especially methoxy or ethoxy, halo $C_{1-6}$alkyl groups, especially —$CF_3$, halo$C_{1-6}$alkoxy, especially —$OCF_3$, —CN, —$CO_2CH_3$, —$NO_2$ and substituted amino especially $C_{1-6}$alkyl and di-$C_{1-6}$alkyl substituted amino, most especially —$NHCH_3$ and —$N(CH_3)_2$ groups. Most especially preferred $R^z$ groups include halogen atoms and optionally substituted $C_{1-6}$alkyl groups as just described.

In another preferred class of compounds of formulae (1), (2a), (2b), (2c) and (2d) in which Y is a group of formula (3b) $R^x$ and/or $R^y$ is a group $-L^1(Alk^1)_n(R^3)_v$ in which n and v is each the integer 1. In this class of compounds $Alk^1$ is preferably an aliphatic chain as defined herein and $R^3$ is a hydrogen atom. Compounds, of this type where -Alk$^1$R$^3$ is an optionally substituted C$_{1-6}$alkyl group, especially a —CH$_3$, —CH$_2$CH$_3$, —CH$_2$CH$_2$CH$_3$, —(CH$_2$)$_3$CH$_3$, —CH(CH$_3$)$_2$, —C(CH$_3$)$_3$, —CH(CH$_2$CH$_3$)$_2$, —CH$_2$CH(CH$_3$)$_2$ or CH$_2$C (CH$_3$)$_3$, an optionally substituted C$_{2-6}$alkenylene, especially —CH$_2$CHCH$_2$ or —CH$_2$CH$_2$CHCH$_2$ or an optionally substituted C$_{2-6}$alkynylene, especially —CH$_2$CCH or —CH$_2$CH$_2$CCH are especially useful. In one preferred group of compounds of this class L$^1$ is a covalent bond. In another preferred group of compounds of this class L$^1$ is a —N(R$^8$)— group, especially an —NH— or —N(CH$_3$)— group. Preferably one of R$^x$ and R$^y$ is a group as just defined and the other is a hydrogen atom or both of R$^x$ and R$^y$ are a group as just defined which may be the same or different.

Particularly preferred optional substituents which may be present on the aliphatic group -Alk$^1$R$^3$ as just defined in substituents R$^x$ and R$^y$ include one, two or three halogen atoms, especially fluorine, chlorine or bromine atoms or C$_{1-6}$alkoxy groups e.g. methoxy or ethoxy, haloC$_{1-6}$alkoxy groups e.g. —OCF$_3$, substituted amino groups e.g. —NHCH$_3$ or —N(CH$_3$)$_2$, —COR$^9$ e.g. —COCH$_3$ or carboxyl (—CO$_2$H) or esterified carboxyl e.g. —CO$_2$CH$_3$ or —CO$_2$C(CH$_3$)$_3$ groups.

In another preferred class of compounds of formulae (1), (2a), (2b), (2c) and (2d) in which Y is a group of formula (3b) R$^x$ and R$^y$ are joined to form a spiro-linked optionally substituted cycloaliphatic or heterocycloaliphatic group [R$^x$ and R$^y$ are joined to the same carbon atom of the ring of formula (3b)]. Especially preferred groups of this type include those spiro-linked optionally substituted cycloaliphatic and heterocycloaliphatic groups described for compounds of formulae (1), (2a), (2b), (2c) and (2d) in which Y is a group of formula (3a).

In one particularly preferred class of compounds of formulae (1), (2a), (2b), (2c) and (2d) in which Y is a group of formula (3b) R$^z$ is a preferred group as just described and R$^x$ and R$^y$ is each a hydrogen atom.

In another particularly preferred class of compounds of formulae (1), (2a), (2b), (2c) and (2d) in which Y is a group of formula (3b) R$^z$ is a preferred group as just described, one of R$^x$ and R$^y$ is a preferred group as just described and the other is a hydrogen atom.

In another particularly preferred class of compounds of formulae (1), (2a), (2b), (2c) and (2d) in which Y is a group of formula (3b) R$^z$ is a preferred group as just described and R$^x$ and R$^y$ is each an -Alk$^1$R$^3$ group as just described.

In another particularly preferred class of compounds of formulae (1), (2a), (2b), (2c) and (2d) in which Y is a group of formulae (3b) R$^z$ is a preferred group as just described and R$^x$ and R$^y$ are joined to form a spiro-linked optionally substituted cycloaliphatic or heterocycloaliphatic group, preferably an optionally substituted cycloaliphatic or heterocycloaliphatic group as just described.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders including inflammation in which the extravasculation of leukocytes plays a role and the invention extends to such a use and to the use of the compounds for the manufacture of a medicament for treating such diseases or disorders.

Diseases or disorders of this type include inflammatory arthritis such as rheumatoid arthritis, vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $R^3$, $L^1$, $L^2$, $Alk^1$, $R^x$, $R^y$, $R^z$ n and v when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2a), (2b), (2c) and (2d).

Thus according to a further aspect of the invention, a compound of formula (1) in which R is a —CO$_2$H group may be obtained by hydrolysis of an ester of formula (1a):

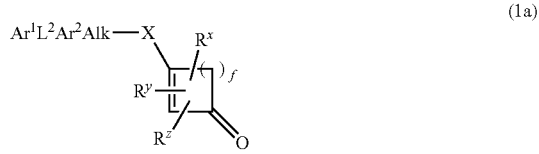

(1a)

where Alk represents a chain:

—CH$_2$CH(CO$_2$Alk$^7$)—, —CH=CH(CO$_2$Alk$^7$)—, or
—CH(CH$_2$CO$_2$Alk$^7$)—

[where Alk$^7$ is for example an alkyl group such as a C$_{1-6}$alkyl group]

The hydrolysis may be performed using either an acid or a base depending on the nature of Alk$^7$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by condensation of a compound of formula (3):

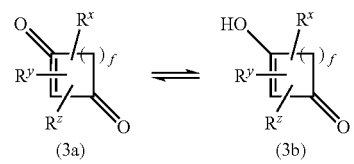

where compounds of formula (3) exist as two tautomeric isomers, (3a) and (3b) in solution with an amine of formula $R^1R^2NH$, an alcohol of formula $R^1OH$ or a thiol of formula $R^1SH$.

The reaction may be performed in an inert solvent or mixture of solvents, for example a substituted amide such as dimethylformamide, an alcohol such as methanol or ethanol, a hydrocarbon such as an aromatic hydrocarbon e.g. benzene or toluene and/or a halogenated hydrocarbon such as 1,2-dichloroethane, or dichloromethane at a temperature from 0° C. to the reflux temperature. Where necessary, for example when a salt of an amine $R^1R^2NH$ is used, an organic base such as diisopropylethylamine can be added.

Any carboxylic acid group present in the intermediate of formula (3) or the amine $R^1R^2NH$, alcohol $R^1OH$ or thiol $R^1SH$ may need to be protected during the displacement reaction, for example as an ethyl ester. The desired acid may then be obtained through subsequent hydrolysis, for example as particularly described above and generally described below.

According to a still further aspect of the invention a compound of formula (1) may also be prepared by condensation of a compound of formula (4) [see below] in which Z represents a leaving group such as a halogen atom, especially a chlorine, bromine or iodine atom, an alkoxy group such as methoxy, ethoxy or isopropoxy, a silyloxy group such as t-butyldimethylsilyloxy, an alkylthio group such as methylthio or ethylthio, an alkylsulphoxide such as methysulphoxide, an aryloxy group such as dinitrophenyloxy or an aralkyloxy group such as benzyloxy, with an amine of formula $R^1R^2NH$, alcohol of formula $R^1OH$ or thiol of formula $R^1SH$.

The reaction may be performed under the reaction conditions just described for condensation of intermediates of formula (3).

Where desired the displacement reaction may also be performed on an intermediate of formulae (3), $R^1R^2NH$, $R^1OH$ or $R^1SH$ which is linked, for example via its R, $R^1$ or $R^3$ group, to a solid support, such as a polystyrene resin. After the reaction the desired compound of formula (1) may be displaced from the support by any convenient method, depending on the original linkage chosen.

Intermediates of formulae (3) $R^1R^2NH$, $R^1OH$ and $R^1SH$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2a), (2b), (2c), and (2d) where appropriate functional groups exist in these compounds.

Thus intermediates of formula (3) may be obtained by hydrolysis of intermediates of formula (4):

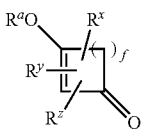
(4)

where $R^a$ represents a $C_{1-6}$alkyl group or a silyl group such as a $^t$butyldimethylsilyl group.

The hydrolysis may be performed using an acid, for example an inorganic acid such as hydrochloric acid in an organic solvent such as an ether e.g. diethylether, or an alcohol e.g. ethanol optionally in the presence of added water at a temperature from about ambient to 80° C.

Intermediates of formula (4) in which f is the integer 1 may be obtained by the cycloaddition of an intermediate of formula (5):

(5)

with a ketene of formula (6):

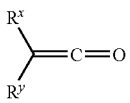
(6)

generated in situ during the cycloaddition reaction from an acid chloride of formula (7):

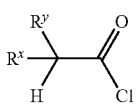
(7)

The reaction may be performed in the presence of an organic base such as an amine e.g. triethylamine or N,N-diisopropylethylamine or a cyclic amine such as pyridine or N-methylmorphidine optionally in an organic solvent such as an ether e.g. diethylether or diisopropylether.

Acid chlorides of formula (7) may be obtained from the corresponding acids by a convenient method of generating acid halides, for example by reaction with thionyl chloride or oxalyl chloride under such standard conditions as are well known in the art.

Intermediate compounds of formula (4) may also be obtained from squaric acid derivations by such well known methods in the art as those of MacDougall, J. M. et al, J. Org. Chem, 64, 5979-83 (1999); Hergueta, R. A., J. Org. Chem., 64, 5979-83, (1999); Heileman, M. J. et al, J. Am. Chem. Soc. 120, 3801-2, (1998); Yamamoto, Y. et al, J. Org. Chem, 62, 1292-8 (1997); Zhag, D. et al, J. Org. Chem. 61, 2594-5 (1996); Petasis, N. A. et al, Synlett, 155-6 (1996); Petasis, N. A. et al, Tetrahedron Lett., 36, 6001-4, (1995); Turnbull, P. et al, J. Org. Chem 60, 644-9 (1995); Yerxa, B. R. et al, Tetrahedron, 50, 6173-80 (1994); Ezcurra, J. E. et al, Tetrahedron Lett, 34, 6177-80, (1993); Ohno, M. et al, Tetrahedron Lett., 34, 4807-10, (1993); Yerxa, B. R. et al, Tetrahedron Lett. 33, 7811-14 (1992); Xu, S. L. et al, J. Org. Chem, 57, 326-8 (1992) and Kravs, J. L. et al, Tetrahedron Lett. 28, 1765-8 (1987).

Further compounds of the invention and intermediates thereto may be prepared by alkylation, arylation or heteroarylation. For example, compounds containing a -L$^1$H or -L$^2$H group (where L$^1$ and L$^2$ is each a linker atom or group) may be treated with a coupling agent $R^3(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoro-methylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Compounds of formula $Ar^1X^1$ may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which, for example, $Ar^1$ represents a 2,6-naphthyridine may be prepared by methods well known to a person skilled in the art, e.g. by the method of Sakamoto, T. et al [Chem. Pharm. Bull. 33, 626-633, (1985)].

Alternatively alkylating agents of formula $Ar^1X^1$ in which, for example, $Ar^1$ represents a 2,6-naphthyridine may be prepared by reaction of a 2,6-naphthyridine N-oxide or N,N'-dioxide with a halogenating agent, e.g. a phosphorous oxyhalide such as phosphorous oxychloride to give a 1-halo or 1,5-dihalo-2,6-napthyridine respectively. In the case of 1,5-dihalo-2,6-napthyridines each halogen atom may be substituted separately by a reagent such as $HL^2Ar^2AlkN(R^2)H$ or $HL^3(Alk^2)_tL^4(R^4)_u$ by the particular methods just described above.

2,6-Napthyridine N-oxides and N,N'-dioxides may be generated from the corresponding 2,6-naphthyridines by the general methods of synthesis of N-oxides described below or they may be synthesised by the methods of Numata, A. et al (Synthesis, 1999, 306-311).

Further alkylating agents of formula $Ar^1X^1$ in which, for example, $Ar^1$ represents a 2,6-naphthyridine, may be prepared by the methods of Giacomello G. et al [Tetrahedron Lett., 1117-1121 (1965)], Tan, R. and Taurins, A. [Tetrahedron Lett., 2737-2744, (1965)], Ames, D. E. and Dodds, W. D. [J. Chem. Soc. Perkin 1, 705-710 (1972)] and Alhaique, F. et al [Tetrahedron Lett., 173-174 (1975)].

Intermediate alcohols of formula $Ar^1OH$ in which $Ar^1$ represents an optionally substituted 2,7-naphthyridin-1-yl group may be prepared by methods well known to a person skilled in the art, e.g. by the method of Sakamoto, T. et al [Chem. Pharm. Bull. 33, 626-633, (1985)] or Baldwin, J, J. et al [J. Org. Chem, 43, 4878-4880, (1978)]. Thus for example the method of Baldwin may be modified to allow the synthesis of intermediate 3-substituted 2,7-naphthyridin-1-yl groups of formula $Ar^1OH$ as depicted in Scheme 1:

Scheme 1

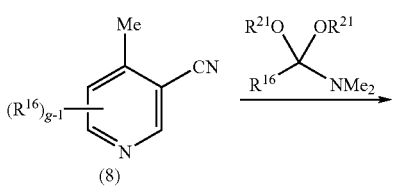

(8)

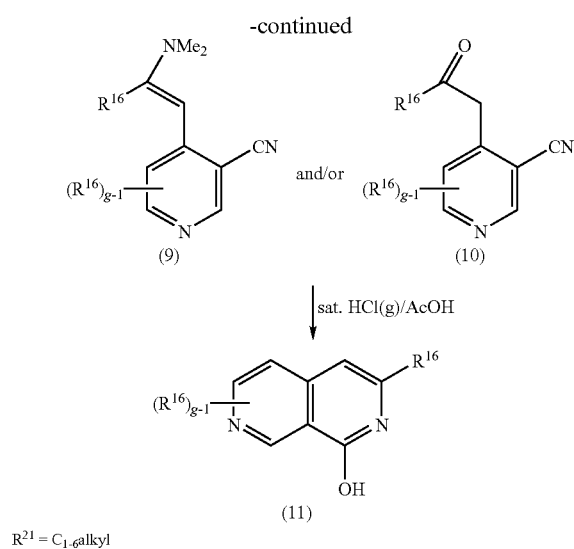

$R^{21} = C_{1-6}alkyl$

Reaction of an optionally substituted 4-methyl-3-cyano pyridine of formula (8) with a N,N-dimethylformamide di-$C_{1-6}$alkyl acetal, e.g. N,N-dimethyl-formamide diethyl acetal, in a dipolar solvent such as an amide e.g. a substituted amide such as dimethylformamide at an elevated temperature e.g. 140-150° gives a compound of formula (9) or (10) or a mixture thereof depending on the nature of the group $R^{16}$.

Compounds of formula (9) or (10) may be cyclised to 3-substituted 2,7-naphthyridin-1-yl alcohol of formula (11) by treatment with an acid e.g. an inorganic acid such as hydrochloric acid or hydrobromic acid or an acidic gas such as hydrogen chloride gas in an organic solvent e.g. an organic acid such as acetic acid optionally in the presence of water at a temperature from about ambient to 50° C.

Alternatively alkylating agents of formula $Ar^1X^1$ in which $Ar^1$ represents an optionally substituted 2,7-naphthyridin-yl group may be prepared by reaction of a 2,7-naphthyridine N-oxide or N,N'-dioxide with a halogenating agent, e.g. a phosphorous oxyhalide such as phosphorous oxychloride to give a 1-halo or 1,6-dihalo- and/or -1,8-dihalo-2,7-napthyridine respectively. In the case of 1,6-dihalo- and/or 1,8-dialo-2,6-napthyridines each halogen atom may be substituted separately by a reagent such as $HL^2Ar^2AlkN(R^2)H$ or $HL^3(Alk^2)_uL^4(R^4)_u$ by the particular methods just described above.

2,7-Napthyridine N-oxides and N,N'-dioxides may be generated from the corresponding 2,7-napthyridines by the general methods of synthesis of N-oxides described below or they may be synthesised by the methods of Numata, A. et al (Synthesis, 1999, 306-311).

Further alkylating agents of formula $Ar^1X^1$ in which, for example, $Ar^1$ represents a 2,7-naphthyridin-1-yl, may be prepared by the methods of Wenkert E. et al J. Am. Chem. Soc. 89, 6741-5 (1967), and Aust. J. Chem. 433 (1972), and Sheffield D. J. J. Chem. Soc. Perkin. Trans I, 2506 (1972).

Intermediate alcohols of formula $Ar^1OH$ in which $Ar^1$ represents a 3-substituted isoquinolin-1-yl group may be prepared by methods well known to a person skilled in the art, e.g. by the methods of Wu M.-J. et al Tetrahedron, 55, 13193-200 (1999), Hiebl J. et al Tetrahedron Lett. 40, 7935-8 (1999), Nagarajan A. et al Indian J. Chem., Sect. B, 28B, 67-78 (1989), Brun E. M. et al Synlett, 7, 1088-90 (1999) and Brun, E. M. et al Synthesis, 273-280 (2000).

Further alkylating agents of formula $Ar^1X^1$ in which, for example, $Ar^1$ represents a isoquinolin-1-yl group, may be prepared by the methods of Falk H. et al Monatsch. Chem. 25, 325-33 (1994), and Deady, L. W. et al Aust. J. Chem 42, 1029-34 (1989).

In a further example intermediates of formula $R^1R^2NH$ may be obtained by reaction of a compound of formula $Ar^1L^2H$ with a compound of formula $X^1Ar^2AlkN(R^2)H$ under the reaction conditions just described Compounds of formula $Ar^1L^2H$ in which, for example $Ar^1$ represents a 2,6-naphthyridine and $L^2$ is a —$N(R^8)$— group, may be prepared from substituted 4-cyano-3-cyanomethylpyridines by the methods of Alhaique, F. et al (ibid and Gazz. Chim. Ital. 1975, 105, 1001-1009) or from 3-fomylpyridines by the methods of Molina, P. at al (Tetrahedron 1992, 48, 4601-4616).

Compounds of formula $Ar^1L^2H$ in which, for example $Ar^1$ represents a 2,7-naphthyridin-1-yl group and $L^2$ is a —$N(R^8)$— group, may be prepared from substituted 4-formylpyridines by the methods of Molina, P. et al Tetrahedron, 48, 4601-4616, (1992), or by the methods described in U.S. Pat. No. 3,938,367.

Compounds of formula $Ar^1L^2H$ in which, for example $Ar^1$ represents a 3-substituted isoquinolin-1-yl group and $L^2$ is a —$N(R^8)$— group, may be prepared by the methods of Bordner, J. et al J. Med. Chem. 31, 1036-9 (1988), Tovar J. D. et al J. Org. Chem., 64, 6499-6504 (1999), Karser E. M. et al Synthesis, 11, 805-6 (1974), and Molino, P et al J. Chem. Soc. Perkin Trans. 1 1727-31 (1990).

In another example, compounds containing a -$L^1H$ or -$L^2H$ or group as defined above may be functionalised by acylation or thioacylation, for example by reaction with one of the alkylating agents just described but in which $X^1$ is replaced by a —$C(O)X^2$, —$C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^1$ is replaced by a —$S(O)Hal$ or —$SO_2Hal$ group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^1H$ or -$L^2H$ group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —CO$_2$R$^5$, —CO$_2$R$^{11}$ or —CO$_2$Alk$^7$ in the compounds may be converted to the corresponding acid [—CO$_2$H] by acid- or base-catalysed hydrolysis depending on the nature of the groups R$^5$, R$^{11}$ or Alk$^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —OR$^5$ or —OR$^{14}$ groups [where R$^5$ or R$^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —OCH$_2$R$^{14}$ group (where R$^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [CO$_2$Alk$^7$ or CO$_2$R$^5$] or aldehyde [—CHO] by reduction, using for example a complex metal hydride such as lithium aluminium hydride or sodium borohydride in a solvent such as methanol.

In another example, alcohol —OH groups in the, compounds may be converted to a corresponding —OR$^5$ or —OR$^{14}$ group by coupling with a reagent R$^5$OH or R$^{14}$OH in a solvent such as tetrahydrofuran in the presence of a phosphine, e.g. triphenylphosphine and an activator such as diethyl-, diisopropyl-, or dimethylazodicarboxylate.

Aminosulphonylamino [—NHSO$_2$NHR$^3$ or —NHSO$_2$NHAr$^1$] groups in the compounds may be obtained, in another example, by reaction of a corresponding amine [—NH$_2$] with a sulphamide R$^3$NHSO$_2$NH$_2$ or Ar$^1$NHSO$_2$NH$_2$ in the presence of an organic base such as pyridine at an elevated temperature, e.g. the reflux temperature.

In another example compounds containing a —NHCSAr$^1$, —CSNHAr$^1$, —NHCSR$^3$ or —CSNHR$^3$ may be prepared by treating a corresponding compound containing a —NHCOAr$^1$, —CONHAr$^1$, —NHCOR$^3$ or —CONHR$^3$ group with a thiation reagent, such as Lawesson's Reagent, in an anhydrous solvent, for example a cyclic ether such as tetrahydrofuran, at an elevated temperature such as the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group L$^1$ or L$^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula Ar$^1$X$^1$ (where X$^1$ is a halogen atom such as a chlorine, bromine or iodine atom) may be converted to such compounds as Ar$^1$CO$_2$R$^{20}$ (in which R$^{20}$ is an optionally substituted alkyl, aryl or heteroaryl group), Ar$^1$CHO, Ar$^1$CHCHR$^{20}$, Ar$^1$CCR$^{20}$, Ar$^1$N(R$^{20}$)H, Ar$^1$N(R$^{20}$)$_2$, for use in the synthesis of for example compounds of formula Ar$^1$L$^2$Ar$^2$AlkN(R$^2$)H, using such well know and commonly used palladium mediated reaction conditions as are to be found in the general reference texts *Rodd's Chemistry of Carbon Compounds*, Volumes 1-15 and Supplementals (Elsevier Science Publishers, 1989), *Fieser and Fieser's Reagents for Organic Synthesis*, Volumes 1-19 (John Wiley and Sons, 1999), *Comprehensive Heterocyclic Chemistry*, Ed. Katritzky et al, Volumes 1-8, 1984 and Volumes 1-11, 1994 (Pergamon), *Comprehensive Organic Functional Group Transformations*, Ed. Katritzky et al, Volumes 1-7, 1995 (Pergamon), *Comprehensive Organic Synthesis*, Ed. Trost and Flemming, Volumes 1-9, (Pergamon, 1991), *Encyclopedia of Reagents for Organic Synthesis*, Ed. Paquette, Volumes 1-8 (John Wiley and Sons, 1995), *Larock's Comprehensive Organic Transformations* (VCH Publishers Inc., 1989) and *March's Advanced Organic Chemistry* (John Wiley and Sons, 5$^{th}$ Ed., 2001).

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

| | |
|---|---|
| NMM—N-methylmorpholine; | EtOAc—ethyl acetate; |
| MeOH—methanol; | BOC—butoxycarbonyl; |
| DCM—dichloromethane; | AcOH—acetic acid; |
| DIPEA—diisopropylethylamine; | EtOH—ethanol; |
| Pyr—pyridine; | Ar—aryl; |
| DMSO—dimethylsulphoxide; | iPr—isopropyl; |
| $Et_2O$—diethylether; | Me—methyl; |
| THF—tetrahydrofuran, | DMF—N,N-dimethylformamide; |
| FMOC—9-fluorenylmethoxycarbonyl; | NBS—N-bromosuccinimide |
| DBU—1,8-Diazabicyclo[5,4-0]undec-7-ene | |
| NCS—N-chlorosuccinimide | |

All NMR's were obtained either at 300 MHz or 400 MHz.

Compounds were named using ACD NamePro version 4.0.

Some intermediates to, and compounds of the invention have restricted rotation about certain bonds resulting in conformational isomers being resolved in proton NMR. Where this is the case resolvable peeks are reported as non-integer numbers of protons reflecting the ratio of rotamers as seen by proton NMR.

Intermediate 1

1-Benzylindoline

Indoline (12.70 g, 106.5 mmol) was dissolved in MeOH (120 ml), stirred at room temperature and treated with potassium carbonate (14.70 g, 106.5 mmol). Benzyl bromide (18.20 g, 106.5 mmol) was then added and the mixture heated to reflux for 4 hr. The solution was cooled and filtered to remove the carbonate. The filtered solution was washed with water (2×100 ml) and extracted into DCM (2×100 ml), dried ($MgSO_4$) and reduced under vacuum to give the title compound (18.65 g, 83%) as a brown semisolid. $\delta H$ ($d^6$ DMSO) 7.27 (5H, br m), 6.98 (1H, t), 6.95 (1H, t), 6.50 (2H, d), 4.18 (2H, s), 3.17 (2H, t, J 7.3 Hz), 2.84 (2H, t, J 7.2 Hz); m/z ($ES^+$, 70V) 210 ($MH^+$).

Intermediate 2

1-Benzyl-5-indolinecarbaldehyde

To a stirred solution of Intermediate 1 (18.65 g, 89.11 mmol) in DMF (100 ml) was added with cooling (cold water bath) phosphorus oxychloride (10.5 ml, 112.4 mmol). The reaction mixture was heated for 2 hr at 100°. The reaction mixture was poured into an ice-water mix (200 ml) and made basic with sodium hydroxide. After cooling overnight the solid formed was collected and dried to give the title compound (20.45 g, 97%) as a brown solid. $\delta H$ ($d^6$ DMSO) 9.59 (1H, s), 7.53 (1H, d), 7.47 (1H, s), 7.31 (5H, m), 6.66 (1H, d), 4.48 (2H, s), 3.54 (2H, t, J 7.2 Hz), 3.02 (2H, t, J 7.3 Hz); m/z ($ES^+$, 70V) 238 ($MH^+$).

Intermediate 3

Methyl (E/Z)-3-(1-benzyl-2,3-dihydro-1H-indol-5-yl)-2-[(benzyloxycarbonyl)amino]-2-propenoate To a stirred solution of Intermediate 3 (1.0 g, 4.21 mmol) and N-(benzyloxycarbonyl)-α-phosphonoglycine trimethyl ester (1.46 g, 4.42 mmol) in DCM (20 ml) was added DBU (0.62 ml, 4.42 mmol). The resultant orange/yellow mixture was stirred for 24 hr. After evaporation the residue was purified by chromatography ($SiO_2$, hexane-$Et_2O$-EtOAc 3:1:1) to give the title compound (1.51 g, 80.1%) as a yellow crystalline solid. $\delta H$ ($d^6$ DMSO) 8.81 (1H, br s), 7.32 (13H, m), 6.55 (1H, s), 5.11 (1H, br s), 4.39 (3H, s), 3.43 (2H, s, J 7.2 Hz), 3.31 (2H, s), 3.29 (2H, s), 2.91 (2H, t, J 7.3 Hz); m/z ($ES^+$, 70V) 443 ($MH^+$).

Intermediate 4

Methyl 2-[(tert-butoxycarbonyl)amino]-3-(2,3-dihydro-1 H-indol-5-yl) propanoate

A stirred solution of Intermediate 3 (1.51 g, 3.41 mmol) and di-tert-butyl dicarbonate (0.78 g, 3.58 mmol) in 1,4-dioxane was hydrogenated at atmospheric pressure with 5% Pd on charcoal (100 mg) for 7 days. The mixture was then hydrogenated again at atmospheric pressure with 20% palladium hydroxide on carbon for 2 days. The catalysts were filtered off and washed with MeOH. After evaporation of the solvents the brown viscous oil was purified by chromatography ($SiO_2$, hexane-EtOAc 2:1) to give the title compound (1.0 g, 91.5%) as a white solid. $\delta H$ ($d^6$ DMSO) 7.15 (1H, d), 6.89 (1H, s), 6.74 (1H, d), 6.39 (1H, d), 5.33 (1H, s), 3.61 (3H, s), 3.38 (2H, t, J 7.3 Hz), 2.86 (2H, t, J 7.2 Hz), 2.81 (1H, d), 2.70 (1H, dd), 1.35 (9H, s); m/z ($ES^+$, 70V) 321 ($MH^+$), 343 ($MNa^+$).

Intermediate 5

Methyl (E/Z)-3-(1-benzyl-2,3-dihydro-1H-indol-5-yl)-2-[(tert-butoxycarbonyl)amino]-2-propenoate To a stirred solution of Intermediate 2 (4.66 g, 19.67 mmol) and N-boc-methyl-2-(dimethylphosphono) glycinate (6.14 g, 20.65 mmol) in DCM (13 ml) was added DBU (2.90 ml, 20.65 mmol) in DCM (5 ml). The resultant orange/yellow mixture was vigorously stirred for 5 hr. After evaporation the residue was purified by chromatography ($SiO_2$; hexane-EtOAc 4:1) to give the title compound (6.42 g, 80%) as a yellow crystalline solid. $\delta H$ ($d^6$ DMSO) 8.30 (1H, br s), 7.44 (1H, br s), 7.34 (6H, m), 6.60 (1H, d), 4.40 (2H, s), 3.70 (3H, s), 3.43 (2H, t, J 7.2 Hz), 2.95 (2H, t, J 7.3 Hz), 1.43 (9H, s); m/z ($ES^+$, 70V) 409 ($MH^+$).

Intermediate 6

Methyl 2-[(tert-butoxycarbonyl)amino]-3-(2,3-dihydro-1H-indol-5-yl) propanoate

A stirred solution of Intermediate 5 (6.0 g, 14.7 mmol) in dry MeOH (60 ml) was hydrogenated at atmospheric pressure with 20% palladium hydroxide on carbon (500 mg) for 24 hr.

The catalyst filtered off and washed with MeOH. After evaporation of the solvent the semi-solid was collected and dried to give the title compound (4.46 g, 95%) as a white solid. δH (d⁶ DMSO) 7.13 (1H, d), 6.87 (1H, s), 6.74 (1H, d), 6.39 (1H, d), 5.33 (1H, s), 3.59 (3H, s), 3.38 (2H, t, J 7.3 Hz), 2.86 (2H, t, J 7.2 Hz), 2.81 (1H, d), 2.70 (1H, dd), 1.35 (9H, s); m/z (ES⁺, 70V) 321 (MH⁺), 343 (MNa⁺).

Intermediate 7

Methyl 2-[(tert-butoxycarbonyl)amino]-3-[1-(3,5-dichloroisonicotinoyl)-2,3-dihydro-1H-indol-5-yl]-propanoate To a stirred solution of Intermediate 6 (600 mg, 1.87 mmol) and 3,5-dichloro-isonicotinoyl chloride (394 mg, 1.87 mmol) in DCM (50 ml) was added DIPEA (0.48 ml, 2.8 mmol) and the resultant mixture stirred for 24 hr. After evaporation of the solvent the oil was collected and dried to give the title compound (911 mg, 98.4%) as a brown oil. SH (d⁶ DMSO) 8.68 (2H, s), 8.11 (1H, d), 7.16 (1H, s), 7.10 (1H, d), 3.82 (2H, t, J 7.2 Hz), 3.70 (3H, s), 3.69 (1H, dd), 3.19 (2H, t, J 7.3 Hz), 3.09 (1H, dd), 2.91 (1H, dd), 1.34 (9H, s); m/z (ES⁺, 70V) 495 (MH⁺).

Intermediate 8

Methyl 2-amino-3-[1-(3,5-dichloroisonicotinoyl)-2,3-dihydro-1H-indol-5-yl]-propanoate A stirred solution of Intermediate 7 (911 mg, 1.84 mmol) in DCM (7 ml) and treated with trifluoroacetic acid (7 ml) and stirred for 1 hr. After this time the solvent was removed. The brown oil was re-dissolved in DCM (30 ml) and was washed with sat. NaHCO₃ (20 ml), dried (MgSO₄), filtered and concentrated to give the title compound (986 mg, 2.5 mmol) as a yellow solid. δH (d⁶ DMSO) 8.83 (2H, s), 8.02 (1H, d), 7.14 (1H, s), 7.07 (1H, d), 3.75 (2H, t, J 7.1 Hz), 3.61 (3H, s), 3.54 (1H, dd), 3.14 (2H, t, J 7.2 Hz), 2.87 (1H, dd), 2.78 (1H, dd); m/z (ES⁺, 70V) 395 (MH⁺).

Intermediate 9

2-tert-Butoxycarbonylamino-3-[1-(2,6-dichloro-pyridine-4-carbonyl)-2,3-dihydro-1H-indol-5-yl]-propionic acid methyl ester The title compound was prepared in a similar manner to Intermediate 7 from 2,6-dichloropyridine-4-carbonyl chloride as a pale yellow foam (99%). δH NMR (CDCl₃) 7.30 (2H, s), 7.19 (1H, s), 6.96 (2H, m), 4.90 (1H, m), 4.48 (1H, m), 3.89 (2H, m), 3.66 (3H, s), 3.08 (2H, t, J 8.1 Hz), 3.02 (2H, m), 1.36 (9H, s); m/z (ES⁺, 70 eV) 516 (M+Na)⁺.

Intermediate 10

2-tert-Butoxycarbonylamino-3-[1-(2,6-dichloro-benzoyl)-2,3-dihydro-1H-indol-5-yl]-propionic acid methyl ester The title compound was prepared in a similar manner to Intermediate 7 from 2,6-dichlorobenzoyl chloride as a colorless oil (99%). δH NMR (CDCl₃) 8.21 (1H, d, J 8.1 Hz), 7.27 (2.6H, m), 6.96 (0.2, s), 6.93 (1H, s), 6.65 (1H, d, J 8.3 Hz), 5.62 (0.2H, d, J 8.3 Hz) 4.91 (1H, m), 4.50 (1H, m), 4.30 (0.4H, t, J 8.0 Hz), 3.73 (1.6H, t, J 8.2 Hz), 3.68 (2.4H, s), 3.61 (0.6H, s), 3.08 (2H, t, J 8.2 Hz), 3.02 (2H, m), 1.36 (7.2H, s), 1.33 (1.8H, s); m/z (ES⁺, 70 eV) 516 (M+Na)⁺.

Intermediate 11

2-tert-Butoxycarbonylamino-3-[1-(Pyridine-4-carbonyl)-2,3-dihydro-1H-indol-5-yl]-propionic acid methyl ester The title compound was prepared in a similar manner to Intermediate 7 from pyridine-4-carbonyl chloride as a yellow foam (99%). δH NMR (CDCl₃) 8.82 (2H, m), 8.05 (1H, m), 7.77 (2H, m), 6.98 (2H, m), 4.91 (1H, m), 4.49 (1H, m), 3.91 (2H, m), 3.67 (3H, s), 3.07 (4H, m), 1.36 (9H, s); m/z (ES⁺, 70 eV) 448 (M+Na)⁺.

Intermediate 12

2-tert-Butoxycarbonylamino-3-[1-(2-chloro-pyridine-3-carbonyl)-2,3-dihydro-1H-indol-5-yl]-propionic acid methyl ester The title compound was prepared in a similar manner to Intermediate 7 from 2-chloropyridine-3-carbonyl chloride as a brown oil (99%). δH NMR (CDCl₃) 8.52 (0.2H, m), 8.47 (1H, m), 8.21 (1H, d, J 8.0 Hz), 7.71 (1H, dd, J 7.5 and 1.8 Hz), 7.35 (0.8H, m), 7.00 (1.6H, m), 6.58 (0.2H, m), 5.65 (0.2H, d, J 8.4 Hz), 4.96 (1H, m), 4.55 (1H, m), 3.82 (2H, m), 3.72 (2.4H, s), 3.67 (0.6H, s), 3.12 (2H, t, J 8.1 Hz), 3.07 (2H, m), 1.41 (7.2H, s), 1.38 (1.8H, s); m/z (ES⁺, 70 eV) 482 (M+Na)⁺.

Intermediate 13

2-Amino-3-[1-(2,6-dichloro-pyridine-4-carbonyl)-2,3-dihydro-1H-indol-5-yl]-propionic acid methyl ester The title compound was prepared from Intermediate 9 in a similar manner to Intermediate 8 as a beige solid (99%). δH NMR (d4 MeOH) 8.08 (1H, d, J 8.2), 7.65 (2H, s), 7.15 (1H, s), 7.09 (1H, d, J 8.2 Hz), 4.02 (2H, t, J 8.2 Hz), 3.70 (1H, m), 3.63 (3H, s), 3.17 (2H, t, J 8.2 Hz), 2.98 (2H, m); m/z (ES⁺, 70 eV) 395 (M+H)⁺.

Intermediate 14

2-Amino-3-[1-(2,6-dichloro-benzoyl)-2,3-dihydro-1H-indol-5-yl]-propionic acid methyl ester The title compound was prepared from Intermediate 10 in a similar manner to Intermediate 8 as a pale yellow foam (61%). δH NMR (d4 MeOH) 8.04 (1H, d, J 8.3 Hz), 7.31 (2.8H, br m), 7.01 (1H, s), 6.97 (0.8H, d, J 8.3 Hz), 6.57 (0.2H, d, J 8.4 Hz), 5.57 (0.2H, d, J 8.4 Hz), 4.17 (2H, m), 3.63 (3H, m), 3.57 (2.4H, s), 3.51 (0.6H, s), 3.04 (2H, m), 2.90 (0.8H, dd, J 13.5 and 6.1 Hz), 2.79 (1H, m), 2.67 (0.2H, dd, J 13.6 and 7.1 Hz). m/z (ES⁺, 70 eV) 395 (M+H)⁺.

Intermediate 15

2-Amino-3-[1-(pyridine-4-carbonyl)-2,3-dihydro-1H-indol-5-yl]-propionic acid methyl ester The title compound was prepared from Intermediate 11 in a similar manner to Intermediate 8 as a light brown oil (59%). δH NMR (d4 MeOH) 8.72 (2H, m), 8.10 (1H, m), 7.61 (2H, m), 7.15 (1H, s), 7.09 (1H, m), 4.02 (2H, m), 3.72 (1H, m), 3.70 (3H, s), 3.16 (2H, t, J 8.2 Hz), 2.97 (2H, m); m/z (ES+, 70 eV) 326 (M+H)+.

Intermediate 16

2-Amino-3-[1-(2-chloro-pyridine-3-carbonyl)-2,3-dihydro-1H-indol-5-yl]propionic acid methyl ester The title compound was prepared from Intermediate 11 in a similar manner to Intermediate 8 as a light brown oil (89%). δH NMR (d4 MeOH) 8.58 (0.2H, m), 8.52 (0.8H, m), 8.15 (0.8H, d, J 8.2 Hz), 7.97 (1H, m), 7.56 (1H, m), 7.15 (1H, s), 7.11 (0.8H, d, J 8.2 Hz), 6.70 (0.2H, m), 5.70 (0.2H, d, J 8.0 Hz), 3.88 (2H, t, J 8.3 Hz), 3.74 (1H, m), 3.71 (2.4H, s), 3.65 (0.6H, s), 3.18 (2H, t, J 8.3 Hz), 2.95 (2H, br m); m/z (ES+, 70 eV) 361 (M+H)+.

EXAMPLE 1

3-[1-(3,5-Dichloroisonicotinoyl)-2,3-dihydro-1H-indol-5-yl]-2-[(3-oxo-spiro [3.5]non-1-en-1-yl)amino]-propanoate To a stirred solution of Intermediate 8 (986 mg, 2.5 mmol) in DCM was added spiro[3.5]nonane-1,3-dione (399 mg, 2.62 mmol) and the resultant solution was stirred for 24 hr. After evaporation of the solvent the crude product was purified by chromatography (SiO$_4$, DCM-MeOH 9:1) to give the title compound (988 mg, 74%) as a pale yellow solid. δH NMR (d$^6$ DMSO) 8.82 (2H, s), 8.01 (0.85H, d) & 5.70 (0.15H, d), 7.18 (1H, s), 7.12 (0.85H, d) & 6.80 (0.15H, d), 4.20 (1H, dd), 3.75 (2H, t, J 7.2 Hz), 3.69 (3H, s), 3.13 (4H, m), 1.57(10H, br m); m/z (ES+, 70V) 529 (MH+).

EXAMPLE 2

3-[1-(3,5-dichloroisonicotinoyl)-2,3-dihydro-1H-indol-5-yl]-2-[(3-oxo-spiro [3.5]non-1-en-1-yl)amino]-propanoic acid A stirred solution of the compound of Example 1 (295 mg, 0.55 mmol) in dioxane-water (1:1) (10 ml) was treated with lithium hydroxide (35 mg, 0.83 mmol). After 1 hr the reaction was concentrated, the residues dissolved in water (4 ml) and to this rapidily stirring solution was added dropwise 10% HCl to precipitate the titled compound (219 mg, 76%) as an off-white solid. δH NMR (d$^6$ DMSO) 8.82 (2H, s), 8.00 (0.82H, d) & 5.69 (0.12H, d), 7.18 (1H, s), 7.14 (0.82H, d) & 6.80 (0.12H, d), 4.07 (1H, dd), 3.75 (2H, t, J 7.2 Hz), 3.13 (3H, m), 2.99 (1H, dd), 1.57(10H, br m); m/z (ES+, 70V) 515 (MH+).

EXAMPLE 3

Methyl 2-[(2-bromo-3-oxo-spiro[3.5]non-1-en-1-yl)amino]-3-[1-(3,5-dichloroisonicotinoyl)-2,3-dihydro-1H-indol-5-yl]-propanoate NBS (69 mg, 3.87 mmol) was added to a stirred solution of the compound of Example 1 (196 mg, 3.71 mmol) in DCM-THF (2:1) (10 ml) at 0° (ice-water bath). After 30 min, the solvent was removed in vacuo and the crude product was purified chromatography (SiO$_2$, EtOAc/hexane, 1:1) to give the title compound (222 mg, 98%) as a transparent oil which solidified on standing. δH NMR (d$^6$ DMSO) 8.83 (2H, s), 8.03 (0.82H, d) & 5.73 (0.12H, d), 7.19 (0.82H, s) & 8.78 (0.12H, s), 7.14 (0.82H, d) & 6.77 (0.12H, d), 4.81 (1H, br m), 3.74 (5H, m), 3.21 (1H, dd), 3.13 (2H, t, J 7.3 Hz), 3.03 (1H, dd), 1.57(10H, br m). m/z (ES+, 70V) 608 (MH+), 630 (MNa+).

EXAMPLE 4

2-[(2-Bromo-3-oxo-spiro[3.5]non-1-en-1-yl)amino]-3-[1-(3,5-dichloroisonicotinoyl)-2,3-dihydro-1H-indol-5-yl]-propanoic acid A stirred solution of the compound of Example 3 (222 mg, 0.36 mmol) in dioxane-water (1:1) (10 ml) was treated with lithium hydroxide (23 mg, 0.54 mmol). After 1 hr. the reaction was concentrated, the residues dissolved in water (4 ml) and to this rapidily stirring solution was added dropwise 10% HCl to precipitate the title compound (150 mg, 69%) as an off-white solid. δH NMR (d$^6$ DMSO) 9.03 (2H, s), 8.24 (0.81H, d) & 5.93 (0.19H, d), 8.98 (0.19H, s) & 7.40 (0.81H, s), 7.35 (0.81H, d) & 6.99 (0.19H, d), 4.92,(1H, m), 3.98 (2H, t, J 7.3 Hz), 3.40 (1H, dd), 3.34 (2H, m), 3.21 (1H, dd), 1.78 (10H, br m); m/z (ES+, 70V) 594 (MH+).

EXAMPLE 5

Methyl 2-[(2-chloro-3-oxo-spiro[3.5]non-1-en-1-yl)amino]-3-[1-(3,5-dichloroisonicotinoyl)-2,3, dihydro-1H-indol-5-yl]-propanoate NCS (53 mg, 3.96 mmol) was added to a stirred solution of the compound of Example 1 (200 mg, 3.78 mmol) in DCM-THF (2:1) (10 ml) at 0° C. (ice-water bath). After 30 min, evaporation of the solvent the crude product was purified by chromatography (SiO$_2$, EtOAc/hexane, 1:1) to give the title compound (203 mg, 95.6%) as a transparent oil which solidified on standing. δH NMR (d$^6$ DMSO) 8.83 (2H, s), 8.04 (0.83H, d) & 5.75 (0.17H, d), 8.78 (0.17H, s) & 7.19 (0.83H, s), 7.14 (0.83H, d) & 6.78 (0.17H, d), 4.70 (1H, m), 3.75 (2H, m), 3.74 (3H, s), 3.21 (1H, dd), 3.13 (2H, m), 3.01 (1H, dd), 1.56 (10H, br m); m/z (ES+, 70V) 563 (MH+), 585 (MNa+).

EXAMPLE 6

2-[(2-Chloro-3-oxo-spiro[3.5]non-1-en-1-yl)amino]-3-[1-(3,5-dichloroisonicotinoyl)-2,3, dihydro-1H-indol-5-yl]-propanoic acid A stirred solution of the compound of Example 5 (203 mg, 0.36 mmol) in dioxane-water (1:1) (10 ml) was treated with lithium hydroxide (22 mg, 0.52 mmol). After 1 hr. the reaction was concentrated, the residues dissolved in water (4 ml) and to this rapidily stirring solution was added dropwise 10% HCl to precipitate the title compound (125 mg, 62%) as an off-white solid. δH NMR (d$^6$ DMSO) 8.81 (2H, s), 8.02 (0.80H, d) & 5.71 (0.20H, d), 8.76 (0.20H, d) & 7.17 (0.80H, s), 7.13 (0.80H, d) & 6.77 (0.20H, d), 4.58 (1H, m), 3.74 (2H, t, J 7.2 Hz), 3.19 (1H, dd), 3.11 (2H, m), 2.98 (1H, dd), 1.55 (10H, br m). m/z (ES+, 70V) 549 (MH+).

EXAMPLE 7

3-[1-(2,6-Dichloro-pyridine-4-carbonyl)-2,3-dihydro-1H-indol-5-yl]-2-(3-oxo-spiro[3.5]non-1-en-1-ylamino)-propionic acid methyl ester The title compound was prepared from Intermediate 13 in a similar manner to the compound of Example 1 as a yellow oil (86%). δH NMR (CDCl$_3$), 8.03 (1H, m), 7.32 (2H, m), 6.92 (2H, m), 5.87 (1H, d, J 7.7 Hz), 4.39 (1H, s), 4.20 (2H, m), 3.91 (1H, m), 3.75 (3H, s), 3.16 (1H, dd, J 13.6 and 4.0

Hz), 3.07 (2H, t, J 8.2 Hz), 2.98 (1H, dd, J 13.6 and 6.4 Hz), 1.59 (10H, br m); m/z (ES+, 70 eV) 528 (M+H)+.

EXAMPLE 8

3-[1-(2,6-Dichloro-benzoyl)-2,3-dihydro-1H-indol-5-yl]-2-(3-oxo-spiro [3.5]non-1-en-1-ylamino)-propionic acid methyl ester The title compound was prepared from Intermediate 14 in a similar manner to the compound of Example 1 as a pale yellow oil (71%). δH NMR (CDCl$_3$) 8.11 (0.8H, d, J 8.1 Hz), 7.20 (2.8H, m), 6.79 (1.8H, m), 6.42 (0.2H, m), 5.70 (0.8H, d, J 7.6 Hz), 5.61 (0.2H, d, J 7.7 Hz), 5.51 (0.2H, d, J 7.8 Hz), 4.44 (0.8H, s), 4.31 (0.2H, s), 4.22 (0.2H, m), 4.13 (1H, m), 4.01 (0.2H, m), 3.65 (2.4H, s), 3.63 (1.8H, m), 3.61 (0.6H, s), 2.96 (4H, br m), 1.50 (10H, br m).); m/z (ES+, 70 eV) 527 (M+H)+.

EXAMPLE 9

2-(3-Oxo-spiro[3.5]non-1-en-1-ylamino)-3-[1-(Pyridine-4-carbonyl)-2,3-dihydro-1H-indol-5-yl]-propionic acid methyl ester The title compound was prepared from Intermediate 15 in a similar manner to the compound of Example 1 as a pale yellow oil (63%). δH NMR (CDCl$_3$) 8.68 (2H, m), 8.09 (1H, br s), 7.35 (2H, m), 6.90 (2H, m), 5.82 (1H, d, J 7.4 Hz), 5.23 (1H, s), 4.42 (1H, m), 4.19 (1H, m), 3.91 (1H, m), 3.75 (3H, s), 3.14 (1H, m), 3.03 (2H, t, J 8.3 Hz), 3.00 (1H, m), 1.56 (10H, br m). m/z (ES+, 70 eV) 460 (M+H)+.

EXAMPLE 10

3-[1-(2-Chloro-pyridine-3-carbonyl)-2,3-dihydro-1H-indol-5-yl]-2-(3-oxo-spiro[3.5]non-1-en-1-ylamino)-propionic acid methyl ester The title compound was prepared from Intermediate 16 in a similar manner to the compound of Example 1 as a pale yellow oil (76%). δH NMR (CDCl$_3$) 8.46 (0.2H, m), 8.42 (0.8H, m), 8.15 (0.8H, d, J 8.1 Hz), 7.70 (1H, m), 7.30 (1H, m), 6.92 (1.8H, m), 6.51 (0.2H, m), 5.83 (1H, m), 5.60 (0.2H, d, J 8.1 Hz), 4.46 (1H, s), 4.32 (0.2H, m), 4.21 (0.8H, m), 3.78 (2H, m), 3.76 (2.4H, s), 3.71 (0.6H, s), 3.16 (1H, m), 3.05 (2H, m), 3.00 (1H, m), 1.55 (10H, br m); m/z (ES+, 70 eV) 494 (M+H)+.

EXAMPLE 11

2-(2-Chloro-3-oxo-spiro[3.5]non-1-en-1-ylamino)-3-[1-(2,6-dichloro-pyridine-4-carbonyl)-2,3-dihydro-1H-indol-5-yl]-propionic acid methyl ester The title compound was prepared from the compound of Example 7 in a similar manner to the compound of Example 5 as a yellow foam (73%) δH NMR (CDCl$_3$) 8.03 (1H, m), 7.32 (2H, s), 6.93 (2H, m), 5.91 (1H, d, J 8.5 Hz), 4.85 (1H, m), 3.91 (2H, m), 3.76 (3H, s), 3.13 (4H, m), 1.49 (10H, br m); m/z (ES+, 70 eV) 562 (M+H)+.

EXAMPLE 12

2-(2-Chloro-3-oxo-spiro[3.5]non-1-en-1-ylamino)-3-[1-(2,6-dichloro-benzoyl)-2,3-dihydro-1H-indol-5-yl]-propionic acid methyl ester The title compound was prepared from the compound of Example 8 in a similar manner to the compound of Example 5 as a white foam (69%). δH NMR (CDCl$_3$) 8.21 (0.8H, m), 7.30 (3H, br m), 6.90 (1.8H, m), 6.51 (0.2H, d, J 8.3 Hz), 5.86 (0.8H, d, J 8.3 Hz), 5.77 (0.2H, d, J 8.4 Hz), 5.61 (0.2H, d, J 8.3 Hz), 4.88 (0.8H, m), 4.78 (0.2H, m), 4.30 (0.4H, m), 3.77 (2.4H, s), 3.74 (0.6H, s), 3.69 (2H, m), 3.17 (2H, m), 3.07 (1.6H, m), 1.46 (10H, br m); m/z (ES+, 70 eV) 561 (M+H)+.

EXAMPLE 13

2-(2-Chloro-3-oxo-spiro[3.5]non-1-en-1-ylamino)-3-[1-(pyridine-4-carbonyl)-2,3-dihydro-1H-indol-5-yl]-propionic acid methyl ester The title compound was prepared from the compound of Example 13 in a similar manner to the compound of Example 5 as a white foam (72%). δH NMR (CDCl$_3$), 8.68 (2H, m), 8.09 (1H, br m), 7.35 (2H, m), 6.92 (2H, m), 5.89 (1H, d, J 8.4 Hz), 4.68 (1H, br m), 3.91 (2H, br m), 3.76,(3H, s), 3.16 (2H, br m), 3.04 (2H, t, J 8.2 Hz), 1.47 (10H, br m); m/z (ES+, 70 eV) 494 (M+H)+.

EXAMPLE 14

2-(2-Chloro-3-oxo-spiro[3.5]non-1-en-1-ylamino)-3-[1-(2-chloro-pyridine-3-carbonyl)-2,3-dihydro-1H-indol-5-yl]-propionic acid methyl ester The title compound was prepared from the compound of Example 10 in a similar manner to the compound of Example 5 as a white foam (85%). δH NMR (CDCl$_3$), 8.62 (0.2H, br m), 8.43 (0.8H, m), 8.15 (0.8H, d, J 8.7 Hz), 7.70 (1H, m), 7.32 (1H, m), 6.91 (1.8H, m), 6.52 (0.2H, m), 6.03 (1H, m), 5.60 (0.2H, dd, J 8.2 and 3.5 Hz), 4.87 (0.8H, m), 4.77 (0.2H, m), 4.25 (0.2H, m), 3.76 (2H, m), 3.76 (2.4H, s), 3.71 (0.6H, s), 3.17 (1.8H, m), 3.06 (2H, m), 1.46 (10H, br m); m/z (ES+, 70 eV) 528 (M+H)+.

EXAMPLE 15

2-(2-Chloro-3-oxo-spiro[3.5]non-1-en-1-ylamino)-3-[1-(2,6-dichloro-pyridine-4-carbonyl)-2,3-dihydro-1H-indol-5-yl]-propionic acid The title compound was prepared from the compound of Example 11 in a similar manner to the compound of Example 2 as a white lyophilised powder (64%). δH NMR (d6 DMSO) 8.80 (1H, d, J 9.6 Hz), 7.98 (1H, d, J 8.2 Hz), 7.85 (2H, s), 7.14 (2H, m), 4.57 (1H, m), 3.96 (2H, t, J 8.2 Hz), 3.21 (1H, dd, J 13.6 and 3.7 Hz), 3.04 (2H, m), 2.92 (1H, dd, J 13.6 and 10.6 Hz), 1.44 (10H, br m), m/z (ES+, 70 eV) 550 (M+H)+.

EXAMPLE 16

2-(2-Chloro-3-oxo-spiro[3.5]non-1-en-1-ylamino)-3-[1-(2,6-dichloro-benzoyl)-2,3-dihydro-1H-indol-5-yl]-propionic acid The title compound was prepared from the compound of Example 12 in a similar manner to the compound of Example 2 as a white lyophilised powder (82%). δH NMR (d6 DMSO), 8.71 (0.8H, J 9.2 Hz), 8.61 (0.2H, d, J 9.5 Hz), 8.05 (0.8H, d, J 8.2 Hz), 7.56 (3H, br m), 7.14 (2H, m), 6.71 (0.2H, d, J 6.9 Hz), 5.51 (0.2H, d, J 8.4 Hz), 4.60 (0.8H, m), 4.49 (0.2H, m), 4.20 (0.4H, m), 3.71 (1.6H, t, J 8.5 Hz), 3.21 (0.8H, m), 3.11 (2H, m), 2.99 (0.8H, dd, J 13.8 and 9.5 Hz), 2.82 (0.2H, dd, J 13.7 and 10.3 Hz) 1.44 (10H, br m); m/z (ES+, 70 eV) 549 (M+H)+.

EXAMPLE 17

2-(2-Chloro-3-oxo-spiro[3.5]non-1-en-1-ylamino)-3-[1-(Pyridine-4-carbonyl)-2,3-dihydro-1H-indol-5-yl]-propionic acid The title compound was prepared from the compound of Example 13 in a similar manner to the compound of Example 2 as a white lyophilised powder (99%). δH NMR (d6 DMSO), 8.73 (2H, m), 7.78 (1H, dd, $J$ 4.3 and 1.5 Hz), 7.61 (1H, m), 7.50 (2H, m), 7.18 (1H, s), 7.05 (1H, d, $J$ 8.2 Hz), 4.58 (1H, m), 4.00 (2H, t, $J$ 8.3 Hz), 3.23 (1H, dd, $J$ 14.1 and 4.8 Hz), 3.06 (3H, m), 1.50 (10H, br m); m/z (ES$^+$, 70 eV) 480 (M+H)$^+$.

EXAMPLE 18

2-(2-Chloro-3-oxo-spiro[3.5]non-1-en-1-ylamino)-3-[1-(2-chloro-pyridine-3-carbonyl)-2,3-dihydro-1H-indol-5-yl]-propionic acid The title compound was prepared from the compound of Example 14 in a similar manner to the compound of Example 2 as a white lyophilised powder (98%). δH NMR (d6 DMSO), 8.75 (0.8H, d, $J$ 9.3 Hz), 8.60 (0.2H, dd, $J$ 4.8 and 1.9 Hz), 8.53 (0.8H, dd, $J$ 4.8 and 1.9 Hz), 8.05 (2H, m), 7.59 (1H, m), 7.18 (1.8H, m), 6.73 (0.2H, d, $J$ 8.5 Hz), 5.51 (0.2H, d, $J$ 8.8 Hz), 4.58 (0.8H, m), 4.49 (0.2H, m), 4.22 (0.4H, m), 3.78 (1.6H, t, $J$ 8.4 Hz), 3.21 (1H, dd, $J$ 13.8 and 4.3 Hz), 3.08 (2H, m), 2.96 (0.8H, dd, $J$ 13.8 and 9.9 Hz), 2.84 (0.2H, m), 1.45 (10H, br m); m/z (ES$^+$, 70 eV) 514 (M+H)$^+$.

EXAMPLE 19

Methyl 3-[1-(3,5-dichloroisonicotinoyl)-2,3, dihydro-1H-indol-5-yl]-2-[(3-oxo-1-cyclopentenyl)amino]-propanoate To a stirred solution of Intermediate 8 (206 mg, 0.52 mmol) in MeNO$_2$ (5 ml) was added cyclopentane-1,3-dione (53 mg, 0.54 mmol), a drop of acetic acid, spatula tip Na$_2$SO$_4$ and the mixture was stirred at 80° for 24 hr. After evaporation of the solvent the crude product was purified by chromatography (SiO$_2$; DCM-MeOH (9:1) to give the title compound (209 mg, 84%) as transparent oil. δH NMR (d$^6$ DMSO) 8.84 (2H, s), 8.05 (0.85H, d) & 5.77 (0.15H, d), 8.75 (0.15H, s) & 7.23 (0.85H, s), 7.17 (0.85H, d) & 6.81 (0.15H, d), 4.80 (1H, s), 4.25 (1H, dd), 3.76 (2H, t, $J$ 7.2 Hz), 3.68 (3H, s), 3.32 (3H, m), 3.02 (1H, dd), 2.5 (2H, m), 2.13 (2H, m); m/z (ES$^+$, 70V) 474 (MH$^+$).

EXAMPLE 20

Methyl 2-[(2-chloro-3-oxo-1-cyclopentenyl)amino]-3-[1-(3,5-dichloroisonicotinoyl)-2,3, dihydro-1H-indol-5-yl]-propanoate The title compound was prepared from the compound of Example 19 in a similar manner to the compound of Example 5 as a transparent oil (123 mg, 93%). δH NMR (d$^6$ DMSO) 8.81 (2H, s), 8.05 (0.85H, d) & 5.75 (0.15H, dd), 8.74 (0.15, d) & 7.24 (0.85H, s), 7.20 (0.85H, d) & 6.84 (0.15H, dd), 4.55 (1H, m), 3.78-3.67 (5H, m), 3.23 (1H, m), 3.13 (3H, m), 2.51 (1H, m), 2.33-2.12 (3H, m); m/z (ES$^+$, 70V) 508 (MH$^+$).

EXAMPLE 21

3-[1-(3,5-dichloroisonicotinoyl)-2,3, dihydro-1H-indol-5-yl]-2-[(3-oxo-1-cyclopentenyl)amino]-propanoic acid The title compound was prepared from the compound of Example 19 in a similar manner to the compound of Example 2 as a white solid (68 mg, 51%). δH NMR (d$^6$ DMSO) 8.84 (2H, s), 8.05 (0.88H, d) & 5.75 (0.12H, d), 8.76 (0.12H, s) & 7.24 (0.88H, s), 7.18 (0.88H, d) & 6.87 (0.12H, d), 4.80 (1H, s), 4.13 (1H, m), 3.77 (2H, t, $J$ 7.2 Hz), 3.24-2.94 (4H, m), 2.47 (2H, m), 2.13 (2H, m); m/z (ES$^+$, 70V) 460 (MH$^+$).

EXAMPLE 22

2-[(2-chloro-3-oxo-1-cyclopentenyl)amino]-3-[1-(3,5-dichloroisonicotinoyl)-2,3, dihydro-1H-indol-5-yl]-propanoic acid The title compound was prepared from the compound of Example 20 in a similar manner to the compound of Example 2 as a white solid (81 mg, 67%). δH NMR (d$^6$ DMSO) 8.82 (2H, s), 8.03 (0.87H, d) & 5.73 (0.13H, d), 8.75 (0.13H, d) & 7.24 (0.87H, s), 7.22 (0.87H, d) & 6.85 (0.13H, d), 4.60 (1H, m), 3.75 (2H, t, $J$ 7.1 Hz), 3.25-3.00 (4H, m), 2.53 (1H, m), 2.33-2.10 (3H, m). m/z (ES$^+$, 70V) 494 (MH$^+$).

EXAMPLE 23

Methyl 3-[1-(3,5-dichloroisonicotinoyl)-2,3, dihydro-1H-indol-5-yl]-2-[(2-isobutyl-3-oxo-1-cyclopentenyl)amino]-propanoate To a stirred solution of Intermediate 8 (209 mg, 0.53 mmol) in MeNO$_2$ (5 ml) was added 2-isobutyl-cyclopentane-1,3-dione (85 mg, 0.55 mmol), a drop of acetic acid, spatula tip Na$_2$SO$_4$ and the mixture was stirred at 80° for 24 hr. After evaporation of the solvent the crude product was purified by chromatography (SiO$_2$; EtOAc) to give the title compound (125 mg, 44%) as a yellow oil. δH NMR (d$^6$ DMSO) 8.81 (2H, s), 8.01 (0.85H, d) & 5.71 (0.15H, d), 8.74 (0.15H, d) & 7.23 (0.85H, s), 7.19 (0.85H, d) & 6.84 (0.15H, d), 4.44 (1H, m), 3.77-3.66 (7H, m), 3.17 (2H, m), 2,37-2.01 (4H, m), 1.89 (2H, d), 1.62 (1H, m), 0.75 (6H, d); m/z (ES$^+$, 70V) 530 (MH$^+$).

EXAMPLE 24

3-[1-(3,5-dichloroisonicotinoyl)-2,3, dihydro-1H-indol-5-yl]-2-[(2-isobutyl-3-oxo-1-cyclopentenyl)amino]-propanoic acid The title compound was prepared from the compound of Example 23 in a similar manner to the compound of Example 2 as a white solid (86 mg, 71%). δH NMR (d$^6$ DMSO) 8.82 (2H, s), 8.00 (0.86H, d) & 5.68 (0.14H, d), 8.75 (0.14H, d) & 7.23 (0.86H, s), 7.21 (0.86H, d) & 6.97 (0.14H, d), 4.32 (1H, m), 3.74 (2H, t, $J$ 7.2 Hz), 3.20-2.91 (4H, m), 2.38-1.91 (4H, m), 1.88 (2H, d), 1.60 (1H, m), 0.74 (6H, d). m/z (ES$^+$, 70V) 516 (MH$^+$).

EXAMPLE 25

Methyl 3-[1-(3,5-Dichloroisonicotinoyl)-2,3-dihydro-1H-indol-5-yl]-2-[(3-oxo-7-oxaspiro[3.5]non-1-en-1-yl)amino]-propanoate To a stirred solution of Intermediate 8 (198 mg, 0.50 mmol) in DCM (5 ml) was added 7-oxa-spiro[3.5]nonane-1,3-dione (81 mg, 0.52 mmol) and the solution was stirred for 24 hr. After evaporation of the solvent the, crude product was purified by chromatography (SiO$_2$; DCM-MeOH, 9:1) to give the title compound (253 mg, 95%) as a yellow solid. δH NMR (d$^6$ DMSO) 8.84 (2H, s), 8.04 (0.86H, d) & 5.73 (0.14H, d), 8.83

(0.14H, d) & 7.20 (0.86H, s), 7.15 (0.86H, d) & 6.81 (0.14H, d), 4.45 (1H, s), 4.26 (1H, dd), 3.79-3.61 (9H, m), 3.15 (2H, m), 3.02 (1H, dd), 1.92 (2H, br m), 1.52 (1H, d), 1.37 (1H, d); m/z (ES$^+$, 70V) 530 (MH$^+$).

EXAMPLE 26

Methyl 2-[(2-Chloro-3-oxo-7-oxaspiro[3.5]non-1-en-1-yl)amino]-3-[1-(3,5-dichloroisonicotinoyl)-2,3,dihydro-1H-indol-5-yl]-propanoate The title compound was prepared from the compound of Example 25 in a similar manner to the compound of Example 5 as a transparent oil (103 mg, 71%). δH NMR (d$^6$ DMSO) 8.82 (2H, s), 8.05 (0.82H, d) & 5.74 (0.18H, d), 8.94 (0.18H, d) & 7.20 (0.82H, s), 7.15 (0.82H, d) & 6.79 (0.18H, d), 4.73 (1H, dd), 3.75 (5H, m), 3.57 (4H, dq, $J$ 7.1 Hz), 3.14 (3H, m), 2.99(1H, dd), 1.99 (2H, br m), 1.15 (1H, d), 1.14 (1H, d); m/z (ES$^+$, 70V) 564 (MH$^+$).

EXAMPLE 27

3-[1-(3,5-dichloroisonicotinoyl)-2,3-dihydro-1H-indol-5-yl]-2-[(3-oxo-7-oxaspiro[3.5]non-1-en-1-yl)amino]-propanoic acid The title compound was prepared from the compound of Example 25 in a similar manner to the compound of Example 2 as a white solid (108 mg, 74%). δH NMR (d$^6$ DMSO) 8.84 (2H, s), 8.04 (0.85H, d) & 5.72 (0.15H, d), 7.20 (0.85H, s) & 8.76 (0.15H, d), 7.16 (0.85H, d) & 6.82 (0.15H, d), 4.12 (1H, dd), 3.77 (2H, m), 3.65 (4H, m), 3.15 (3H, m), 2.99(1H, dd), 1.95 (2H, m), 1.50 (1H, d), 1.35 (1H, d); m/z (ES$^+$, 70V) 516 (MH$^+$).

EXAMPLE 28

2-[(2-Chloro-3-oxo-7-oxaspiro[3.5]non-1-en-1-yl)amino]-3-[1-(3,5-dichloroisonicotinoyl)-2,3, dihydro-1H-indol-5-yl]-propanoic acid The title compound was prepared from the compound of Example 26 in a similar manner to the compound of Example 2 as a white solid (23 mg, 24%). δH NMR (d$^6$ DMSO) 8.82 (2H, s), 8.03 (0.82H, d) & 5.73 (0.18H, d), 8.78 (0.18H, s) & 7.19 (0.82H, s), 7.14 (0.82H, d) & 6.78 (0.18H, d), 4.60 (1H, dd), 3.75 (2H, m), 3.56 (4H, m), 3.13 (3H, m), 2.99(1H, dd), 1.98 (2H, m), 1.48 (1H, d), 1.26 (1H, d); m/z (ES$^+$, 70V) 550 (MH$^+$).

EXAMPLE 29

3-[1-(3,5-Dichloroisonicotinoyl)-2,3-dihydro-1H-indol-5-yl]-2-[(4,4-dimethyl-3-oxo-1-cyclobutenyl)amino]-propanoate To a stirred solution of Intermediate 8 (195 mg, 0.49 mmol) in DCM (5ml) was added 2,2-dimethyl-1,3-cyclobutanedione (58 mg, 0.47 mmol) and the solution stirred for 24 hr. After evaporation of the solvent the crude product was purified by chromatography (SiO$_2$; DCM-MeOH, 9:1) to give the title compound (212 mg, 88%) as a brown solid. δH NMR (d$^6$ DMSO) 8.84 (2H, s), 8.05 (0.86H, d) & 5.74 (0.14H, d), 8.76 (0.14H, d) & 7.20 (0.86H, s), 7.15 (0.86H, d) & 6.81 (0.14H, d), 4.39 (1H, s), 4.26 (1H, dd), 3.76 (2H, m), 3.72 (3H, s), 3.16 (3H, m), 3.03 (1H, dd), 1.10 (3H, s), 1.04 (3H, s); m/z (ES$^+$, 70V) 488 (MH$^+$).

EXAMPLE 30

Methyl 2-[(2-chloro-4,4-dimethyl-3-oxo-1-cyclobutenyl)amino]-3-[1-(3,5-dichloroisonicotinoyl)-2,3-dihydro-1H-indol-5-yl]-propanoate The title compound was prepared from the compound of Example 29 in a similar manner to the compound of Example 5 as a transparent oil (130 mg, 78%). δH NMR (d$^6$ DMSO) 8.82 (2H, s), 8.05 (0.84H, d) & 5.76 (0.16H, d), 7.20 (1H, s), 7.15 (0.84H, d) & 6.79 (0.16H, d), 4.73 (1H, dd), 3.74 (5H, m), 3.14 (3H, m), 3.05 (1H, dd), 1.13 (3H, s), 1.05 (3H, s); m/z (ES$^+$, 70V) 522 (MH$^+$).

EXAMPLE 31

3-[1-(3,5-Dichloroisonicotinoyl)-2,3-dihydro-1H-indol-5-yl]-2-[(4,4-dimethyl-3-oxo-1-cyclobutenyl)amino]-propanoic acid The title compound was prepared from the compound of Example 29 in a similar manner to the compound of Example 2 as a white solid (64 mg, 63%). δH NMR (d$^6$ DMSO) 8.84 (2H, s), 8.04 (0.87H, d) & 5.73 (0.13H, d), 8.76 (0.13H, d) & 7.20 (0.87H, s), 7.16 (0.87H, d) & 6.82 (0.13H, d), 4.38 (1H, s), 4.13 (1H, dd), 3.77 (2H, t, $J$ 8.3 Hz), 3.15 (3H, m), 3.01 (1H, dd), 1.11 (3H, s), 1.05 (3H, s). m/z (ES$^+$, 70V) 474 (MH$^+$).

EXAMPLE 32

2-[(2-chloro-4,4-dimethyl-3-oxo-1-cyclobutenyl)amino]-3-[1-(3,5-dichloroisonicotinoyl)-2,3-dihydro-1H-indol-5-yl]-propanoic acid The title compound was prepared from the compound of Example 30 in a similar manner to the compound of Example 2 as a white solid (78 mg, 61%). δH NMR (d$^6$ DMSO) 8.82 (2H, s), 8.02 (0.88H, d) & 5.73 (0.12H, d), 8.74 (0.12H, d) & 7.19 (0.88H, s), 7.13 (0.88H, d) & 6.80 (0.12H, t), 4.56 (1H, br m), 3.74 (2H, t, $J$ 8.1 Hz), 3.11 (4H, m), 0.82 (3H, s), 0.80 (3H, s). m/z (ES$^+$, 70V) 508 (MH$^+$).

EXAMPLE 33

Methyl 3-[1-(3,5-Dichloroisonicotinoyl)-2,3-dihydro-1H-indol-5-yl]-2-[(3-oxo-5-propyl-1-cyclohexenyl)amino]-propanoate To a stirred solution of Intermediate 8 (202 mg, 0.51 mmol) in MeNO$_2$ (5 ml) was added 5-propyl-cyclohexane-1,3-dione (83 mg, 0.53 mmol), a drop of acetic acid, spatula tip Na$_2$SO$_4$ and the mixture stirred at 80° for 24 hr. After evaporation of the solvent the crude product was purified by chromatography (SiO$_2$; DCM-MeOH, 9:1) to give the title compound (253 mg, 92%) as transparent oil. δH NMR (d$^6$ DMSO) 8.84 (2H, s), 8.05 (1H, d), 7.23 (2H, m), 7.17 (1H, d), 4.75 (1H, s), 4.26 (1H, m), 3.76 (2H, m), 3.72 (3H, s), 3.16 (2H, m), 3.06 (2H, m), 2.15 (2H, m), 1.85 (2H, m), 1.29 (4H, m), 0.87 (3H, m); m/z (ES$^+$, 70V) 530 (MH$^+$).

EXAMPLE 34

Methyl 2-[(2-chloro-5-propyl-3-oxo-1-cyclohexenyl)amino]-3-[1-(3,5-dichloroisonicotinoyl)-2,3-dihydro-1H-indol-5-yl]-Propanoate The title compound was prepared from the compound of Example 29 in a similar manner to the compound of Example 5 as a transparent oil (140 mg, 97%). δH NMR (d$^6$ DMSO)

8.82 (2H, s), 8.03 (0.84H, d) & 5.74 (0.16H, d), 8.73 (0.16H, d) & 7.20 (2H, m), 7.15 (0.84H, d) & 6.81 (0.16H, d), 4.72 (1H, dd), 3.77-3.68 (5H, m), 3.21 (1H, dd), 3.13 (2H, t), 3.02 (1H, dd), 2.29 (2H, m), 1.89 (2H, m), 1.55 (1H, m), 1.18 (3H, m), 0.83 (3H, m); m/z (ES$^+$, 70V) 564 (MH$^+$).

EXAMPLE 35

3-[1-(3,5-Dichloroisonicotinoyl)-2,3-dihydro-1H-indol-5-yl]-2-[(3-oxo-5-propyl-1-cyclohexenyl) amino]-propanoic acid The title compound was prepared from the compound of Example 33 in a similar manner to the compound of Example 2 as a white solid (96.2 mg, 72%). δH NMR (d$^6$ DMSO) 8.84 (2H, s), 8.05 (1H, d), 7.24 (2H, m), 7.18 (1H, d), 4.82 (1H, s), 4.10 (1H, br m), 3.77 (2H, t, J 7.1 Hz), 3.16 (3H, t), 3.07 (1H, dd), 2.99 (1H, dd), 2.14 (2H, m), 1.89 (2H, m), 1.28 (4H, m), 0.87 (3H, m); m/z (ES$^+$, 70V) 516 (MH$^+$).

EXAMPLE 36

2-[(2-chloro-5-propyl-3-oxo-1-cyclohexenyl)amino]-3-[1-(3,5-dichloroisonicotinoyl)-2,3-dihydro-1H-indol-5-yl]-propanoic acid The title compound was prepared from the compound of Example 34 in a similar manner to the compound of Example 2 as a white solid (114.7 mg, 74.5%). δH NMR (d$^6$ DMSO) 8.82 (2H, s), 8.03 (0.86H, d) & 5.74 (0.14H, d), 8.97 (0.15H, d) & 7.20 (2H, m), 7.15 (0.86H, d) & 6.80 (0.14H, d), 4.62 (1H, dd), 3.76 (2H, t, J 7.3 Hz), 3.21 (1H, dd), 3.13 (2H, t), 3.02 (1H, dd), 1.23-0.76 (8H, m), 1.04 (3H, s). m/z (ES$^+$, 70V) 550 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R$^{4507}$) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY Cell Adhesion to MAdCAM-Ig

This assay was performed in the same manner as the α$_4$β$_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the α$_4$β$_1$ integrin assay.

α$_5$β$_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention such as the compounds of the Examples generally have IC$_{50}$ values in the α$_4$β$_1$ and assay of 1 μM and below and in the α$_4$β$_7$ assay of 5 μM and below. In the other assays featuring α integrins of other subgroups the same compounds had IC$_{50}$ values of 50 μM and above thus demonstrating the potency and selectivity of their action against α$_4$ integrins.

The invention claimed is:

1. A compound of formula (1)

(1)

wherein
R$^1$ is a group Ar$^1$L$^2$Ar$^2$Alk- in which Ar$^1$L$^2$ is isonicotinoyl or in which Ar$^1$ is selected from the group consisting of pyridyl, dichloropyridyl, and indole;
L$^2$ is a covalent bond or a linker atom or group L$^{2a}$ or a linker -(Alk$^3$)$_d$L$^{2a}$-;
L$^{2a}$ is a —O— or —S— atom or —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— group [where R$^8$ is a hydrogen atom or a straight or branched C$_{1-6}$alkyl group], Alk$^3$ is a straight or branched chain C$_{1-6}$alkylene;

d is zero or the integer 1;

Ar$^2$ is an optionally substituted bicyclic heteroarylene group in which the optional substituents are selected from one or two halogen atoms, or C$_{1-6}$alkyl, halo C$_{1-6}$alkyl, C$_{1-6}$alkoxy, haloC$_{1-6}$alkoxy, —CN, —CO$_2$CH$_3$, —NO$_2$, amino, —NR$^5$R$^6$ and —N(R$^5$)COCH$_3$ groups;

R$^5$ is a hydrogen atom, or a C$_{1-6}$alkyl or C$_{3-8}$cycloalkyl group;

R$^6$ is as defined for R$^5$;

Alk is a chain —CH$_2$—CH(R)—, or —CH(CH$_2$R)—;

R is a carboxylic acid (—CO$_2$H) or a —CO$_2$Alk$^7$ or —CONR$^5$R$^6$ derivative or tetrazole, phosphonic acid, phosphinic acid, sulphonic acid, sulphinic acid, boronic acid or acylsulphonamide biostere thereof;

Alk$^7$ is a straight or branched C$_{1-8}$alkyl, C$_{2-8}$alkenyl, C$_{2-8}$alkynyl, C$_{3-8}$cycloalkyl, C$_{3-8}$cycloalkylC$_{1-8}$alkyl, C$_{3-8}$heterocycloalkylC$_{1-6}$alkyl, C$_{1-6}$alkyloxyC$_{1-6}$alkyl, C$_{1-6}$alkylthioC$_{1-6}$alkyl, C$_{1-6}$alkylsulfinylC$_{1-6}$alkyl, C$_{1-6}$alkylsulfonylC$_{1-6}$alkyl, C$_{3-8}$cycloalkyloxy C$_{1-6}$alkyl, C$_{3-8}$cycloalkylthioC$_{1-6}$alkyl, C$_{3-8}$cycloalkylsulfinylC$_{1-6}$alkyl, C$_{3-8}$cycloalkylsulfonylC$_{1-6}$alkyl, C$_{1-6}$alkyloxycarbonylC$_{1-6}$alkyl, C$_{1-6}$alkyloxycarbonylC$_{1-6}$alkenyl, C$_{1-6}$alkyloxycarbonyloxyC$_{1-6}$alkyl, C$_{1-6}$alkyloxycarbonyloxyC$_{1-6}$alkenyl, C$_{3-8}$cycloalkyloxycarbonyloxyC$_{1-6}$alkyl, N-di-C$_{1-8}$alkylamino C$_{1-8}$alkyl, N—C$_{6-12}$aryl-N—C$_{1-6}$alkylaminoC$_{1-6}$alkyl, N-di-C$_{1-8}$alkyl-carbamoylC$_{1-8}$alkyl, C$_{6-10}$ arylC$_{1-6}$alkyl, C$_{6-10}$aryl, C$_{6-10}$aryloxyC$_{1-8}$alkyl, C$_{6-12}$arylthioC$_{1-8}$alkyl, C$_{6-12}$arylsulfinylC$_{1-8}$alkyl, C$_{6-12}$arylsulfonylC$_{1-8}$alkyl, C$_{1-8}$alkanoyloxyC$_{1-8}$alkyl, C$_{4-8}$imido C$_{1-8}$alkyl, or C$_{6-12}$aroyloxyC$_{1-8}$alkyl group or a triglyceride;

X is an —N(R$^2$)— group;

R$^2$ is a hydrogen atom or a C$_{1-6}$alkyl group;

R$^z$ is an atom or group -L$^1$(Alk$^1$)$_n$R$^3$; L$^1$ is a covalent bond or a —O— —S— or —Se—atom or —N(R$^8$)— group; Alk$^1$ is a straight or branched C$_{1-6}$alkylene chain; R$^3$ is a hydrogen or halogen atom or an optionally substituted C$_{1-8}$alkyl, C$_{3-10}$heterocycloaliphatic, C$_{6-12}$aromatic group or C$_{1-9}$heteroaromatic group; n is zero or the integer 1;

optional substituents which may be present on the C$_{1-8}$alkyl group represented by R$^3$ include halogen atoms, C$_{1-6}$alkoxy groups, haloC$_{1-6}$alkoxy groups, —CN, —CO$_2$CH$_3$, —NO$_2$, —NR$^5$R$^6$ or phenyl;

optional substituents which may be present on the C$_{3-10}$heterocycloaliphatic group represented by R$^3$ include the optional substituents as described for the spiro linked R$^x$, R$^y$ C$_{3-10}$heterocycloaliphatic group;

optional substituents which may be present on the C$_{6-12}$aromatic group or C$_{1-9}$heteroaromatic group represented by R$^3$ include halogen atoms, or C$_{1-6}$alkyl, haloC$_{1-6}$alkyl, C$_{1-6}$alkoxy or halo C$_{1-6}$alkoxy groups;

R$^x$ and R$^y$ are joined together to form an optionally substituted spiro linked C$_{3-10}$cycloaliphatic or C$_{3-10}$heterocycloaliphatic group;

optional substituents which may be present on such spiro linked C$_{3-10}$cycloaliphatic groups include halogen atoms, C$_{1-6}$alkyl groups, C$_{1-6}$alkoxy groups, halo C$_{1-6}$alkoxy groups, —CN, —CO$_2$CH$_3$, —NO$_2$, —NHCH$_3$ and —N(CH$_3$)$_2$ groups;

optional substituents which may be present on such spiro linked heterocycloaliphatic groups include halogen atoms, C$_{1-6}$alkyl groups, C$_{1-6}$alkoxy groups, haloC$_{1-6}$alkoxy groups, —CN, —CO$_2$CH$_3$, —NO$_2$, —NHCH$_3$ and —N(CH$_3$)$_2$ groups; when the spiro linked heterocycloaliphatic group contains a nitrogen atom this may be substituted by a group —(L$^6$)$_p$(Alk5)$_q$R$^{12}$ where L$^6$ is —C(O)— or —S(O)$_2$—, Alk$^5$ is a C$_{1-6}$alkylene chain, and R$^{12}$ is a hydrogen atom or an phenyl ring; p is zero or an integer 1; q is zero or an integer 1;

f is the integer 1;

and the salts and N-oxides thereof.

2. A compound according to claim 1 in which R is a carboxylic acid (—CO$_2$H) group.

3. A compound according to claim 1 in which R is an esterified carboxyl group of formula —CO$_2$Alk$^7$.

4. A compound according to claim 1 in which R$^2$ is a hydrogen atom.

5. A compound according to claim 1 in which Ar$^2$ is an optionally substituted indolediyl or indolinediyl group.

6. A compound according to claim 1 in which Ar$^1$ is an optionally substituted pyridyl, group.

7. A compound according to claim 1 of formula (2a):

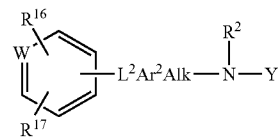

(2a)

wherein —W═ is —CH═, —N═, or —N(O)═ group;

R$^{16}$ and R$^{17}$, which may be the same or different are each a hydrogen atom or an halogen atom or C$_{1-6}$alkyl, halo C$_{1-6}$alkyl, C$_{1-6}$alkoxy or haloC$_{1-6}$alkoxy group;

Y is a group of formula

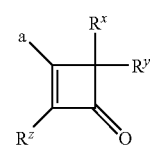

(3a)

where a indicates the point of attachment of the group —N(R$^2$)—;

and the salts, and N-oxides thereof.

8. A compound according to claim 7 in which W is a —N═ atom or —N(O)═ group.

9. A compound according to claim 1 of formula (2b):

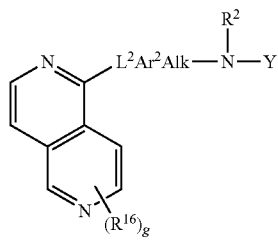

(2b)

wherein g is the integer 1, 2, 3 or 4;
each $R^{16}$ which may be the same or different is a hydrogen atom or an halogen atom or $C_{1-6}$alkyl, halo$C_{1-6}$alkyl, $C_{1-6}$alkoxyl, halo$C_{1-6}$alkoxy, —CN, —$CO_2CH_3$, —$NO_2$, —$NH_2$, —$NR^5R^6$, —$N(R^5)COCH_3$, phenyl, furyl, thienyl, imidazolyl, pyridyl or pyrimidinyl group;
Y is a group of formula

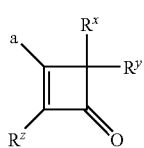

(3a)

and the salts and N-oxides thereof.

10. A compound according to claim 1 of formula (2c):

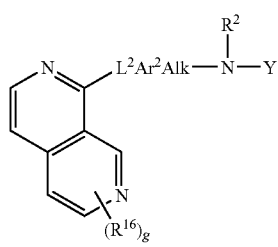

(2c)

wherein g is the integer 1, 2, 3 or 4;
each $R^{16}$ which may be the same or different is a hydrogen atom or an halogen atom or $C_{1-6}$alkyl, halo$C_{1-6}$alkyl, $C_{1-6}$alkoxyl, halo$C_{1-6}$alkoxy, —CN, —$CO_2CH_3$, —$NO_2$, —$NH_2$, —$NR^5R^6$, —$N(R^5)COCH_3$, phenyl, furyl, thienyl, imidazolyl, pyridyl or pyrimidinyl group;
Y is a group of formula

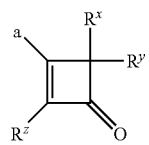

(3a)

and the salts and N-oxides thereof.

11. A compound according to claim 1 of formula (2d):

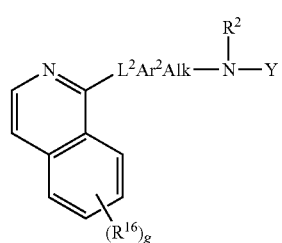

(2d)

wherein g is the integer 1, 2, 3 or 4;
each $R^{16}$ which may be the same or different is a hydrogen atom or an halogen atom or $C_{1-6}$alkyl, halo$C_{1-6}$alkyl, $C_{1-6}$alkoxyl, halo$C_{1-6}$alkoxy, —CN, —$CO_2CH_3$, —$NO_2$, —$NH_2$, —$NR^5R^6$, —$N(R^5)COCH_3$, phenyl, furyl, thienyl, imidazolyl, pyridyl or pyrimidinyl group;
Y is a group of formula

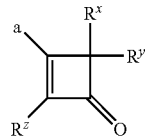

(3a)

and the salts and N-oxides thereof.

12. A compound according to claim 1 in which $Ar^2$ is an optionally substituted 1,4-indolediyl, 1,5-indolediyl, 1,4-indolinediyl or 1,5-indoleinediyl group.

13. A pharmaceutical composition comprising a compound according to claim 1 together with one or more pharmaceutically acceptable carriers, excipients or diluents.

* * * * *